US008641672B2

(12) United States Patent
Yodfat et al.

(10) Patent No.: US 8,641,672 B2
(45) Date of Patent: Feb. 4, 2014

(54) INFUSION AND SENSING DEVICE WITH BATTERY CHARGING AND DATA TRANSFERRING MECHANISMS

(75) Inventors: Ofer Yodfat, Modi'in (IL); Avihoo P. Keret, Kfar Vradim (IL); Avraham Neta, Misgav (IL); Illai Gescheit, Tel Aviv (IL); Tsabar Mor, Naharia (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 532 days.

(21) Appl. No.: 12/921,824

(22) PCT Filed: Mar. 10, 2009

(86) PCT No.: PCT/IL2009/000266
§ 371 (c)(1),
(2), (4) Date: Sep. 10, 2010

(87) PCT Pub. No.: WO2009/113060
PCT Pub. Date: Sep. 17, 2009

(65) Prior Publication Data
US 2011/0009824 A1 Jan. 13, 2011

Related U.S. Application Data

(60) Provisional application No. 61/035,288, filed on Mar. 10, 2008.

(51) Int. Cl.
A61M 1/00 (2006.01)
(52) U.S. Cl.
USPC .......................................... 604/151

(58) Field of Classification Search
USPC ........................................... 604/151
See application file for complete search history.

(56) References Cited

U.S. PATENT DOCUMENTS

| 3,418,552 A | 12/1968 | Holmes |
| 3,631,847 A | 1/1972 | Hobbs, II |
| 3,771,694 A | 11/1973 | Kaminski |
| 3,840,795 A | 10/1974 | Roszyk et al. |
| 3,939,391 A | 2/1976 | Winnacker |

(Continued)

FOREIGN PATENT DOCUMENTS

| WO | WO 2007/052277 A1 | 5/2007 |
| WO | WO 2008/024812 A2 | 2/2008 |

OTHER PUBLICATIONS

International Search Report, PCT Application No. PCT/IL2009/000266, date of mailing Jan. 29, 2010 (6 pgs.).

(Continued)

*Primary Examiner* — Jason Flick
(74) *Attorney, Agent, or Firm* — Mintz Levin Cohn Ferris Glovsky and Popeo, P.C.

(57) ABSTRACT

Disclosed is a portable ambulatory fluid delivery device. The device includes a dispensing unit to dispense therapeutic fluid, the dispensing unit including one or more rechargeable batteries, a housing to retain the one or more rechargeable batteries, a reservoir to contain the therapeutic fluid, a driving mechanism to cause delivery of the therapeutic fluid from the reservoir to a user's body, and at least one electrical connector to be coupled to a recharging unit to direct electrical power received from the recharging unit to recharge the one or more rechargeable batteries. At least a portion of the housing is securable to a skin of the user.

25 Claims, 24 Drawing Sheets

(56) References Cited

U.S. PATENT DOCUMENTS

| | | |
|---|---|---|
| 4,065,712 A | 12/1977 | Godard et al. |
| 4,374,354 A | 2/1983 | Petrovic et al. |
| 4,498,843 A | 2/1985 | Schneider et al. |
| 4,544,369 A | 10/1985 | Skakoon et al. |
| 4,657,486 A | 4/1987 | Stempfle et al. |
| 4,942,352 A | 7/1990 | Sano |
| 5,157,319 A | 10/1992 | Klontz et al. |
| 5,225,763 A | 7/1993 | Krohn et al. |
| 5,299,571 A | 4/1994 | Mastrototaro |
| 5,376,070 A | 12/1994 | Purvis et al. |
| 5,390,671 A | 2/1995 | Lord et al. |
| 5,391,250 A | 2/1995 | Cheney, II et al. |
| 5,482,473 A | 1/1996 | Lord et al. |
| 5,680,028 A | 10/1997 | McEachern |
| 5,771,438 A | 6/1998 | Palermo et al. |
| 5,912,925 A | 6/1999 | Palermo et al. |
| 5,957,895 A | 9/1999 | Sage et al. |
| 5,982,764 A | 11/1999 | Palermo et al. |
| 6,459,882 B1 | 10/2002 | Palermo et al. |
| 6,485,461 B1 | 11/2002 | Mason et al. |
| 6,565,509 B1 | 5/2003 | Say et al. |
| 6,589,229 B1 | 7/2003 | Connelly et al. |
| 6,723,072 B2 | 4/2004 | Flaherty et al. |
| 6,740,059 B2 | 5/2004 | Flaherty |
| 7,142,811 B2 | 11/2006 | Terranova et al. |
| 7,144,384 B2 | 12/2006 | Gorman et al. |
| 7,254,366 B2 | 8/2007 | Palermo et al. |
| 8,137,314 B2 * | 3/2012 | Mounce et al. ............... 604/151 |
| 2003/0054703 A1 | 3/2003 | Fischer et al. |
| 2007/0106218 A1 | 5/2007 | Yodfat et al. |
| 2007/0191702 A1 | 8/2007 | Yodfat et al. |
| 2008/0215035 A1 | 9/2008 | Yodfat et al. |
| 2010/0137802 A1 | 6/2010 | Yodfat et al. |
| 2010/0145276 A1 | 6/2010 | Yodfat et al. |
| 2010/0211011 A1 * | 8/2010 | Haar ............................. 604/151 |
| 2011/0130716 A1 * | 6/2011 | Estes et al. ...................... 604/66 |

OTHER PUBLICATIONS

Diabetes Medicine 2006; 23(2):141-147, Comparison of the effects of continuous subcutaneous insulin infusion (CSII) and NPH-based multiple daily insulin injections (MDI) on glycaemic control and quality of life: results of the 5 nations trial.

Boizel, R., "Glucose monitoring and pump data management software operated on a personal digital assistant can contribute to improve diabetes control in CSII-treated patients", *Diabetes Metab.*, 33:314-315 (2007).

Hoogma et al., "Comparison of the effects of continuous subcutaneous insulin infusion (CSII) and NPH-based multiple daily insulin injections (MDI) on glycaemic control and quality of life: results of the 5-nations trial", *Diabetes Med.*, 23(2):141-147 (2007).

Parkner et al., "Overnight CSII as supplement to oral antidiabetic drugs in Type 2 diabetes", *Diabetes Obes. Metab.*, 10:556-563 (2007).

\* cited by examiner

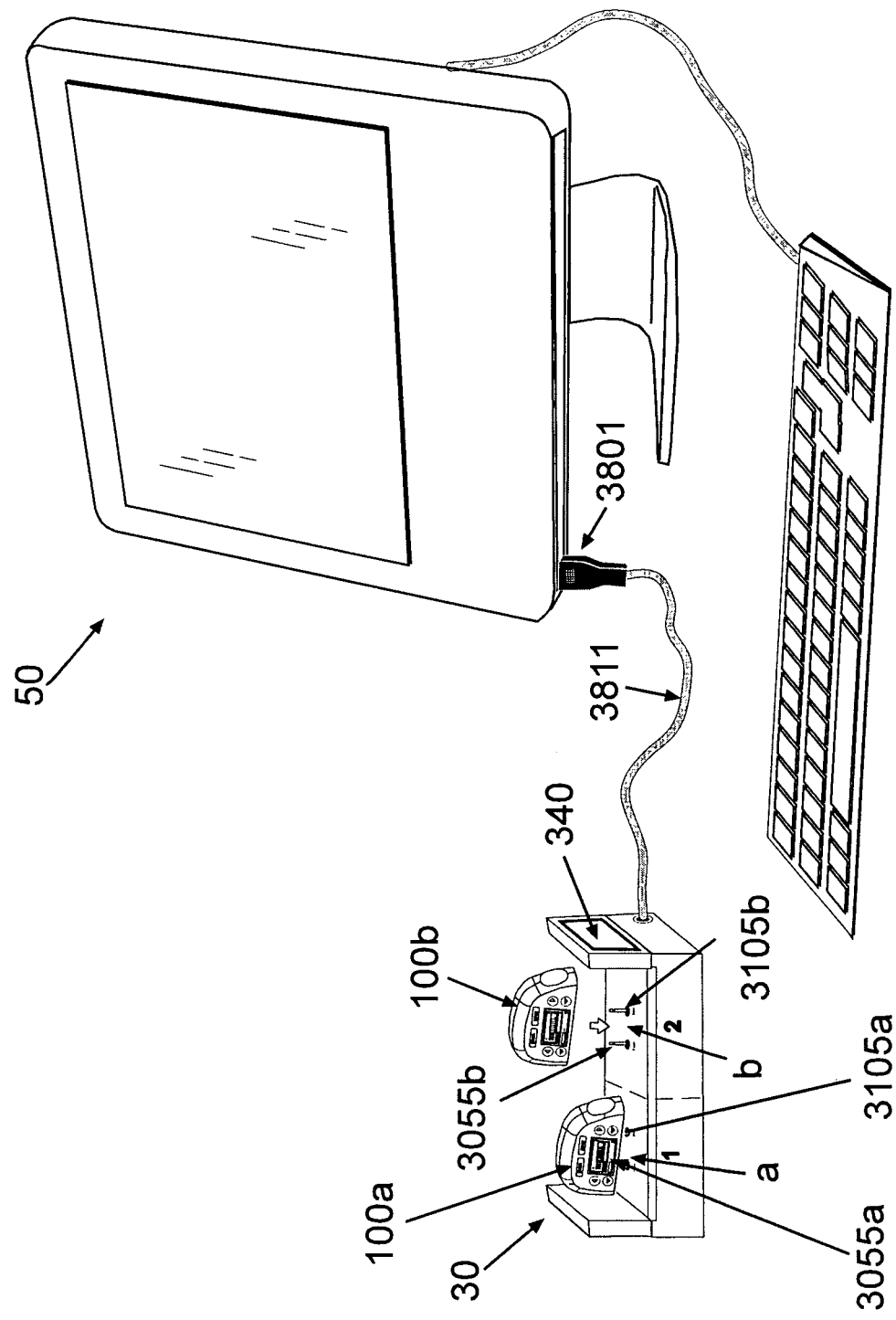

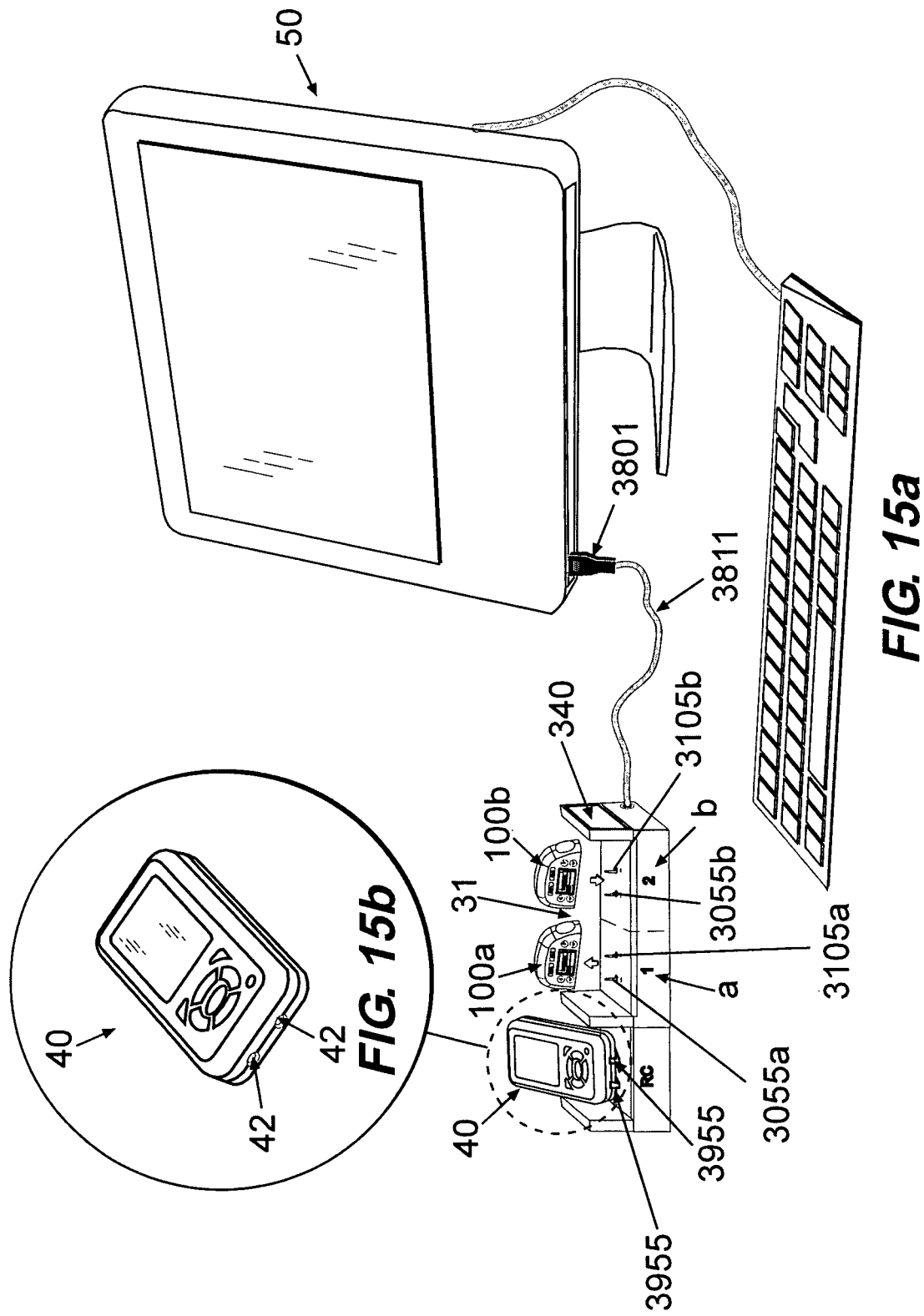

INFUSION AND SENSING DEVICE WITH BATTERY CHARGING AND DATA TRANSFERRING MECHANISMS

CROSS-REFERENCE TO RELATED APPLICATIONS

The present application is a 35 U.S.C. 371 national stage entry of PCT/IL2009/000266, which has an international filing date of Mar. 10, 2009 and claims priority to U.S. Provisional Patent Application No. 61/035,288, filed in the U.S. Patent & Trademark Office on Mar. 10, 2008. The present application incorporates herein by reference the disclosure of each of the above-referenced applications in its entirety.

FIELD

Embodiments of the present disclosure relate generally to a system, a device and a method for sustained medical infusion of fluids and/or continuous monitoring of body analyte. More particularly, the present disclosure is directed to systems, devices and methods that include a device that comprises a portable dispenser and/or an analyte sensor powered by rechargeable energy storage cell and mechanisms to recharge the batteries and transfer data.

BACKGROUND

Diabetes and Insulin Pumps

Medical treatment of several illnesses/conditions requires continuous drug infusion into various body compartments, for example, through subcutaneous and intra-venous injections. Patient suffering from Diabetes mellitus (DM), for example, require the administration of varying amounts of insulin throughout the day to control their blood glucose levels. In recent years, ambulatory portable insulin infusion pumps have emerged as an alternative to multiple daily syringe injections of insulin, initially for Type 1 diabetes patients (see, for example, Diabetes Medicine 2006; 23(2): 141-7) and subsequently for Type 2 (see, for example, Diabetes Metab 2007 Apr. 30, Diabetes Obes Metab 2007 Jun. 26). Such pumps, which deliver insulin at a continuous and/or periodic basal rates as well as in bolus volumes, were developed to liberate patients from having to perform repeated self-administered injections, and to enable them to maintain a near-normal daily routine. Both basal and bolus volumes have to be delivered in substantially precise doses, according to individual prescription, because an overdose or under-dose of insulin could be fatal.

Insulin Pump Generations

The first generation of portable insulin pumps included "pager like" devices each having a reservoir contained within a housing. A long tube delivered insulin from the pump attached to a patient's belt to a remote insertion site. The reservoir, delivery tube and the hypodermic cannula together constituted an "infusion set". With these first-generation devices it is recommended that they be replaced every 2-3 days to avoid local infection at the cannula insertion site. Such devices are disclosed, for example, in U.S. Pat. Nos. 3,631,847 3,771,694, 4,657,486 4,544,369, the contents of all of which are hereby incorporated by reference in their entireties. These devices represent a significant improvement over multiple daily injections, but tend to be relatively large in size and in weight. Additionally, these devices generally require long tubing, making the device somewhat bulky and cumbersome to wear and carry. One reason for the relatively large weight and size of these devices is the large sized batteries (e.g., of AA or AAA-type) required for meeting the high energy demand of the motor, screen, alarms, and other power consuming components of the devices.

The bulkiness of first generational insulin pump devices (in part because of the long tubing used) harms the devices popularity with many diabetic insulin users because these devices disturb users' regular activities, e.g., sports activities, like swimming.

To avoid the tubing limitation, a new concept for a second generation was proposed. The new concept was based on a remote controlled skin adherable device with a housing having a bottom surface adapted for contact with the patient's skin, with a reservoir contained within the housing, and with an injection needle adapted to be in fluid communication with the reservoir. These skin securable (e.g., adherable) devices are designed to be replaced every 2-3 days, similarly to the currently available pump infusion sets. However, many patients prefer to extend this period until reservoir emptying. The second-generation paradigm is described, for example, in U.S. Pat. Nos. 4,498,843, 5,957,895, 6,589,229, 6,740,059, 6,723,072, and 6,485,461, the contents of all of which are hereby incorporated by reference in their entireties. Second-generation skin securable devices generally require that the entirety of the devices be disposed-of every 3 days, or so, thus resulting in some of the more expensive components (e.g., electronics, driving mechanism) being discarded. Additionally, a remote controlled skin securable device tends to be heavy and bulky, thus creating an impediment for maintaining daily activity. Here too, one reason for the large size and heavy weight of second generation devices is their sizes and the relatively large number of batteries they each hold to supply energy to the devices' motors, alarms, communication mechanisms used to maintain a communication link between the skin securable devices and the remote controls, etc. In U.S. Pat. No. 7,144,384, the content of which is hereby incorporated by reference in its entirety, a skin adherable device is disclosed: In one embodiment, a large portion of the device's volume is occupied by four (4) Silver-Oxide button batteries positioned perpendicularly to the longitudinal axis of the device, making the device thick (18 mm) and bulky. Moreover, the heavy and bulky batteries used with such insulin pump devices typically last for only 3 days, thus requiring the user to discarded the expensive device typically every 3 days.

A third generation ($3^{rd}$ gen.) skin adherable device was developed to avoid the price constraints associated with earlier generations and to extend patient customization. An example of such a device is described in previously filed patent application Ser. No. 11/397,115 and PCT International Application No. PCT/IL06/001276, owned by Medingo, the contents of both these applications is hereby incorporated by reference in their entireties. A third generation device includes a remote control unit and a skin securable (e.g., adherable) patch unit that includes two parts:

A first portion (e.g., a "reusable part") containing a metering portion, electronics, and other relatively expensive components.

A second portion (e.g., "disposable part") containing the reservoir retaining therapeutic fluid (e.g., insulin) and, in some embodiments, batteries. The disposable part also includes a tube to deliver the fluid from the reservoir to an outlet port that contains a connecting lumen.

The third-generation device concept provides a cost-effective skin adherable infusion device and enables diverse usage with different reservoir sizes, different needle and cannula types, etc.

Continuous Glucose Monitors (CGM) and Closed Loop System

Continuous sensing of bodily analytes within the interstitial fluid of the subcutaneous (SC) tissue is described, for example, in U.S. Pat. Nos. 5,390,671, 5,391,250, 5,482,473, 5,299,571, and 6,565,509, the contents of all of which are hereby incorporated by reference in their entireties. These sensing devices each includes, in some embodiments, a subcutaneous probe and a sensing unit that contains a processing unit and energy supply. In previously filed U.S. patent application Ser. No. 11/706,606, entitled "Systems and methods for sensing analyte and dispensing therapeutic fluid", the content of which is hereby incorporated by reference in its entirety, an insulin dispenser and a glucose sensor are disclosed that are contained within one skin adhered unit that is provided with a reusable part and a disposable part. In such a dual function device, a closed loop system may be implemented where insulin is dispenses based on, at least in part, sensed glucose levels (artificial pancreas). In some embodiments, the batteries reside in the reusable part of this dual unit.

Pump and Sensors Batteries Recharging

A first generation infusion pump powered by rechargeable batteries is described in U.S. Pat. No. 5,225,763 to Krohn et al., the content of which is hereby incorporated by reference in its entirety. The batteries can be recharged by a base unit connected to AC power. Under some circumstances, the pump operation of such a device might have to be suspended during charging. This may be unacceptable for, insulin pump users because stopping the delivery of insulin may be detrimental to the users' health.

Use of rechargeable batteries in second generation skin adherable pumps is of less importance because the entire device is generally disposed-of every few days (insulin pump are usually disposed-of every 2-3 days). Moreover, batteries recharging cannot be done during operation because the device is connected to the user's body.

In third generation devices, the skin-securable units, each comprises a reusable part and a disposable part. If the battery (ies) resides in the reusable part it can be recharged. A patient may use two reusable parts so that when one reusable part is operating the second one is being recharged.

In a continuous glucose monitor (CGM) or in a CGM with insulin dispenser that includes a reusable part and a disposable part, batteries can reside in the reusable part and be recharged when another reusable part is operating.

Pumps and Sensors Data Downloading

Pump log file, recording and maintaining information regarding insulin delivery, have to periodically be downloaded to a PC to be used, for example, in delivery programs tailoring.

A first generation insulin pump enables data downloading during pump operation is described, for example, in U.S. Pat. No. 5,376,070, the content of which is hereby incorporated by reference in its entirety. The pump may be connected to a communication station and data may be transferred from the pump using, for example, optical coupling. In embodiments of such apparatus, the user is tied, in effect, to the communication station to avoid drug delivery interruption.

Data downloading in second generation pumps may be performed wirelessly to a remote control. In the event of remote control loss or malfunction, the data stored in the pump and stored data in the remote control may be lost.

In third generation insulin pumps, having reusable and disposable parts, data transfer from one reusable part can be done while another reusable part is operating.

SUMMARY

Embodiments according to the present disclosure describe a device that includes a skin securable (e.g., adherable) dispensing unit (also referred to as the "patch unit" or "dispensing unit") and a remote control unit (e.g., a unit not directly connected or integrated to the dispensing unit). The patch unit can include an analyte sensor, and therapeutic fluid can be dispensed according to sensed analyte levels (closed-loop system). The dispensing unit may include at least one battery that can be recharged. In some embodiments, the dispensing unit may include a disposable part and a reusable part. The disposable part may include a drug reservoir and outlet port and the reusable part may include relatively expensive components, for example, electronics and driving mechanism(s). In some embodiments, the rechargeable batteries are contained in the reusable part and may have relatively thin dimensions (e.g., less than 5 mm). Examples of suitable batteries having such dimension include batteries manufactured by Excellatron Solid State, LLC, U.S.

In some embodiments, during operation of one reusable part, the batteries of a second reusable part can be recharged. The patch unit, which may include reusable and disposable parts, contains an insulin dispenser and/or glucose sensor. After 2-3 days of usage, the disposable part is replaced and the recharged reusable part becomes operative and coupled to another disposable part. A fully charged reusable part may have, in some embodiments, enough power stored in its batteries to operate the dispensing unit for at least three days. During this time, the depleted reusable part (i.e., the reusable part that was previously operating while the now used reusable part was being recharged), with respect to which the power stored in its batteries is not sufficient to enable typical operation of the dispensing device for three days, is recharged (i.e., its rechargeable batteries are charged).

According to some embodiments, a device is provided that delivers therapeutic fluid and is provided with at least one battery and a mechanism for recharging the at least one battery and transfer data. In some embodiments, the recharging and data transfer operations may operate substantially concomitantly.

According to some embodiments, a device is provided that delivers therapeutic fluid and can monitor bodily analytes, and is provided with at least one battery and a recharging mechanism to recharge the at least one battery and to concomitantly transfer data.

According to some embodiments, a device is provided that is configured to deliver insulin and includes at least one rechargeable battery and a recharging mechanism to recharge the at least one battery. Such a device may also include a data transfer mechanism to concomitantly transfer data.

According to some embodiments, a device is provided that delivers insulin and can monitor glucose levels and is provided with at least one battery, a mechanism to recharge the at least one battery and transfer data. Such a device may perform these various functions substantially concomitantly.

According to some embodiments, a device is provided that delivers insulin and is provided with at least one battery, and a mechanism to recharge the at least one battery that includes an internal power source. Battery recharging could thus be performed without interruption with normal operations and without the need of another power source.

According to some embodiments, a device is provided that delivers insulin and is provided with at least one battery and a mechanism to recharge the at least one battery. Battery recharging can be done without interruption with normal operation.

Further, according to some embodiments, a device is provided that delivers insulin and can monitor glucose levels, and includes at least one battery and one or more mechanisms to recharge the at least one battery and to concomitantly transfer data. Battery recharging and data transferring may be done without interruption with normal operation of the device.

Additionally, according to some embodiments, a device is provided that includes a skin securable (e.g., adherable) dispensing unit that delivers insulin and can monitor glucose levels, and includes at least one battery and a one or more mechanisms to recharge the at least one battery and to substantially concomitantly transfer data.

According to some embodiments, a device is provided that includes a skin securable dispensing unit to deliver insulin and which includes at least one rechargeable battery and one or more mechanisms to recharge the at least one battery and to substantially concomitantly transfer data. The dispensing unit may include a reusable part and a disposable part, and the at least one battery may be located in the reusable part.

According to some embodiments, a device is provided that includes a skin securable dispensing unit to deliver insulin and which can monitor glucose levels, and is provided with at least one battery and one or more mechanisms to recharge the at least one battery and substantially concomitantly transfer data. The dispensing unit may include a reusable part and a disposable part and the at least one battery may be located in the reusable part.

In some embodiments, a skin securable dispensing unit that includes at least one battery and one or more mechanisms to recharge the at least one battery is provided.

In some embodiments, a two-part dispensing patch unit and one or more mechanisms to charge batteries disposed in the reusable part is provided.

In some embodiments, a recharging unit is provided. The recharging unit can substantially concomitantly supply power to at least one patch unit and/or at least one reusable part, and to the remote control unit. The recharging unit can be powered by an AC/DC voltage converter and/or by at least one battery. Recharging can be performed with magnetic induction, i.e., a primary winding in the recharging unit that is electrically coupled to a secondary winding in the dispensing unit.

In some embodiments, the recharging unit includes a data transfer mechanism to and from at least one patch unit and/or the at least one reusable part. Data can be transferred by, for example, magnetic induction, an RF link, etc.

In some embodiments, the dispensing unit or the reusable part contains a USB connector that includes a power supply and a data transfer mechanism with any USB host (e.g., a PC).

The term USB host refers to mechanism, device, system, etc., configured to supply power and transfer data through the same connection, such as Host Controller Device (HCD), TS connectors, TRS connectors, PS/2 connectors, Mini-DIN connector, Universal Host Controller Interface (UHCI), USB On The Go, etc.

The term PC (personal computer) refers to an electrical device that includes a USB host, including, but not limited to, personal computers, PDAs, cellular phones, USB hubs and the like.

In some embodiments, a portable recharging unit that can control the dispensing unit is disclosed. The recharging unit includes a user interface (e.g., LCD display and operating buttons) configured to receive commands from a user and provide information to the user. The connection between the recharging unit and the dispensing unit can be a wired-connection (e.g., USB) and/or a wireless connection.

In one aspect, a portable ambulatory fluid delivery device is disclosed. The device includes a dispensing unit to dispense therapeutic fluid, the dispensing unit including one or more rechargeable batteries, a housing to retain the one or more rechargeable batteries, a reservoir to contain the therapeutic fluid, a driving mechanism to cause delivery of the therapeutic fluid from the reservoir to a user's body, and at least one electrical connector to be coupled to a recharging unit to direct electrical power received from the recharging unit to recharge the one or more rechargeable batteries. At least a portion of the housing is securable to a skin of the user.

Embodiments of the device may include one or more of the following features.

The device may further include the recharging unit.

The dispensing unit may further include a communication module to communicate data signals representative of data relating to operation of the dispensing unit, the communication module being configured to communicate the data signals substantially concomitantly with receipt of the electrical power from the recharging unit.

The at least one electrical connector of the dispensing unit may include a USB connector configured to direct the electrical power and the data signals.

The communication module may include a wireless transceiver to establish a communication link with an external remote controller communicating the data signals.

The at least one electrical connector may include at least one transducer configured to be electromagnetically coupled to a second transducer disposed in the recharging unit. The second transducer may be configured to cause inductive transfer of the electrical power from the second transducer to the first transducer. The inductively transferred electrical power may include a power signal modulated based on data relating to operation of the dispensing unit.

The dispensing unit may further include a communication module to demodulate and determine, based on the modulated power signal, the data relating to the operation of the dispensing unit.

The at least one electrical connector may include at least one dedicated recharging electrical terminal to receive the electrical power from the recharging unit, and at least one dedicated data terminal to perform bi-directional communication of data relating to operation of the dispensing unit.

The dispensing unit may include a first portion having at least a portion of the driving mechanism, a communication module, the at least one electrical connector and the one or more rechargeable batteries, and a second portion having a reservoir containing the therapeutic fluid. The dispensing unit may be operable upon connection of the first portion and the second portion. The at least one electrical connector may be connectable to the recharging unit when the first portion is disconnected from the second portion. The first portion may include a reusable part of the dispensing unit and the second portion may include a disposable part of the dispensing unit.

The device may further include a cradle unit configured to adhere to the skin of the user. The dispensing unit may be connectable and disconnectable to and form the cradle unit.

The device may further include a remote control unit configured to communicate with the dispensing unit.

The dispensing unit may be configured to perform one or more of, for example, dispensing the therapeutic fluid to the user and/or sensing analyte levels of the user while the one or more batteries are charged by the recharging unit.

In another aspect, a recharging device to recharge a fluid delivery device is disclosed. The recharging device includes at least one electrical connector configured to couple to at least a part of a portable ambulatory dispensing unit of the fluid delivery device to provide electrical power to the dispensing unit to recharge one or more rechargeable batteries disposed in the dispensing unit, and a charger to direct the electrical power from a power source to the at least one electrical connecter. The charger is further configured to alter the electrical power directed from the power source.

Embodiments of the recharging device may include one or more of the features described above in relation to the fluid delivery device, as well as any of the following features.

The device may further include a communication module to communicate data signals representative of data relating to operation of the dispensing unit.

The at least one electrical connector may be configured to provide the electrical power substantially concomitantly with communication of the data signals through the communication module.

The at least one electrical connector may include a first electrical connector configured to be coupled to the dispensing unit, and at leak one other electrical connector to be coupled to another dispensing unit.

The at least one electrical connector may be configured to couple to at least a part of a remote control unit of the fluid delivery device.

The communication module may be configured to receive data from the dispensing unit and transmit the received data to another dispensing unit.

The recharging device may further include a storage device to store data relating to operation of the dispensing unit.

The at least one electrical connector may include at least one transducer configured to cause inductive transfer of the electrical power from the at, least one transducer to another transducer disposed in the dispensing unit.

The inductively transferred electrical power may include a power signal. The recharging device may further include a communication module to modulate the power signal based on data relating to operation of the dispensing unit such that a communication module of the dispensing unit can determine, based on the inductively transferred modulated power signal, the data relating to the operation of the dispensing unit.

The recharging device may further include a portable power source including at least one battery to generate at least a portion of the electrical power directed to the dispensing unit.

The recharging device may further include a housing containing the at least one electrical connector. The housing may be configured to be substantially stationary such that when at least part of the dispensing unit is coupled to the at least one electrical connector, fluid delivery by the dispensing unit is suspended.

The recharging device may further include a portable housing containing the at least one electrical connector such that the at least one electrical connector in the portable housing is configured to be coupled to the at least the part of the dispensing unit while the dispensing unit is operating.

The at least one electrical connector may be configured to couple to a first portion of a dispensing unit, the first portion retaining the one or more rechargeable batteries. The dispensing unit may be operable upon connection of the first portion and at least another portion.

The recharging device may be configured to operate in accordance with EN-IEC 60602 standard.

In a further aspect, a method for recharging a portable ambulatory dispensing unit of a fluid delivery device is disclosed. The method includes providing the dispensing unit, the dispensing unit having one or more rechargeable batteries to store energy to power the dispensing unit and at least one electrical connector, providing a recharging device having at least one electrical connector, coupling at least a part of the dispensing unit to the recharging device so that the at least one electrical connector of the dispensing unit is in electrical communication with the at least one electrical connector of the recharging device, and directing electrical power from the recharging device to the dispensing unit to recharge the one or more rechargeable batteries.

Embodiments of the method may include one or more of the features described above in relation to the fluid delivery device and the recharging device, as well as any of the following features.

The method may further include communicating data signals representing data relating to operation of the dispensing unit between the dispensing unit and the recharging device.

The method may further include communicating the data signals to another dispensing unit coupled to the recharging device.

The method may further include storing data signals representing data relating to operation of the dispensing unit on a storage device of the recharging device.

Directing the electrical power to the dispensing unit may include inductively transferring electrical power from a first transducer of the recharging device to a second transducer of the dispensing unit.

Inductively transferring electrical power may include inductively transferring a power signal, modulating the power signal based on data relating to operation of the dispensing unit, and determining, based on the inductively transferred modulated power signal, the data relating to the operation of the dispensing unit.

Directing electrical power may include directing electrical power to recharge a first portion of the dispensing unit, the first portion having the one or more rechargeable batteries to store energy to power the dispensing unit.

The method may further include coupling at least another dispensing unit to the recharging device and communicating data signals between the dispensing unit and the at least other dispensing unit.

The method may further include coupling at least one remote control unit to the recharging device and directing electrical power to the at least one remote control unit.

In yet another aspect, a therapeutic delivery system is disclosed. The system includes a dispensing unit including a disposable part connectable to one of two or more reusable parts, each of the two or more reusable parts having one or more rechargeable batteries to store energy to power the dispensing unit and a recharging device configured to recharge at least one of the two or more reusable parts while another of the two or more reusable parts is connected to the disposable part.

Embodiments of the system may include one or more of the features described above in relation to the fluid delivery device, the recharging device and the method, as well as any of the following features.

The recharging device may further be configured to charge an external remote controller configured to generate control signals to control one or more of operation of the dispensing unit and operation of a glucose sensor to sense analyte levels of a patient, the glucose sensor being coupled to the therapeutic delivery system.

The recharging device may include a communication module to communicate data signals with at least one of, for example, the dispensing unit, a personal computer and/or an external remote controller configured to generate control signals to control operation of the dispensing unit.

The recharging device may be configured to recharge the at least one of the two or more reusable parts by one of, for example, an inductive coupling element and/or an electrical conduction element.

In another aspect, a therapeutic fluid delivery system is discloses. The system includes a recharging device to recharge a dispensing unit having a disposable part connectable to one of two or more reusable parts, each of the two or more reusable parts having one or more rechargeable batteries to store energy to power the dispensing unit, the recharging device including at least one electrical connector to direct electrical power to recharge at least one of the two or more reusable parts while another of the two or more reusable parts is connected to the disposable part.

Embodiments of the fluid delivery system may include one or more of the features described above in relation to the fluid delivery device, the recharging device, the method and the first-described system, as well as any of the following features.

The at least one electrical connector may include at least one inductive coupling element, the at least one inductive coupling element configured to cause inductive transfer of electrical power from the at least one inductive coupling element to corresponding inductive coupling elements disposed in each of the two or more reusable parts.

The at least one electrical connector of the recharging device may include at least one electrical terminal to mechanically and electrically couple with corresponding complementary at least one electrical terminal in each of the two or more reusable parts.

The at least one electrical connector of the recharging device may include at least one dedicated recharging electrical terminal to direct output power, and at least one dedicated data terminal to communicate data signals representative of the data relating to operation of the dispensing unit.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIGS. 14a-e are views and diagrams depicting exemplary replacement operations of a depleted reusable part of a dispensing unit with a recharged reusable part.

FIGS. 15a-b are diagrams depicting an exemplary recharging and synchronizing unit connectable to two reusable parts, a remote control and a PC.

DETAILED DESCRIPTION

Disclosed are systems, devices and methods for recharging a rechargeable dispensing unit that dispenses therapeutic fluid. In some embodiments, a portable ambulatory fluid delivery device is disclosed. The device includes a dispensing unit to dispense therapeutic fluid, the dispensing unit including one or more rechargeable batteries, a housing to retain the one or more rechargeable batteries, a reservoir to contain the therapeutic fluid, a driving mechanism to cause delivery of the therapeutic fluid from the reservoir to a user's body, and at least one electrical connector to be coupled to a recharging unit to direct electrical power received from the recharging unit to recharge the one or more rechargeable batteries. At least a portion of the housing is securable to a skin of the user. Recharging the one or batteries may thus be performed with the batteries disposed in the dispensing unit (i.e., it is not necessary to remove the batteries from the dispensing unit to have them recharged.) In some embodiments, the one or more batteries are recharged while the portable device continues to operate, thus avoiding any interruptions in the delivery of therapeutic fluid (e.g., insulin) to the patient. The dispensing unit may include a communication module to communicate data signals representative of data relating to operation of the dispensing unit substantially concomitantly with receipt of electrical power from the recharging unit. For example, in some implementations, power transfer may be implemented through inductive transfer of electrical power in which a power signal transferred between the recharging unit and the fluid delivery device is modulated based on the data relating to operation of the dispensing unit.

In some embodiments, a recharging device to recharge a fluid delivery device includes at least one electrical connector configured to couple to at least a part of a dispensing unit of the fluid delivery device to provide electrical power to the dispensing unit to recharge one or more rechargeable batteries disposed in the dispensing unit. In some embodiments, the recharging device is configured to direct electrical power to recharge at least one of two or more reusable parts while another of the two or more reusable parts is connected to the disposable part.

Figure 1A:
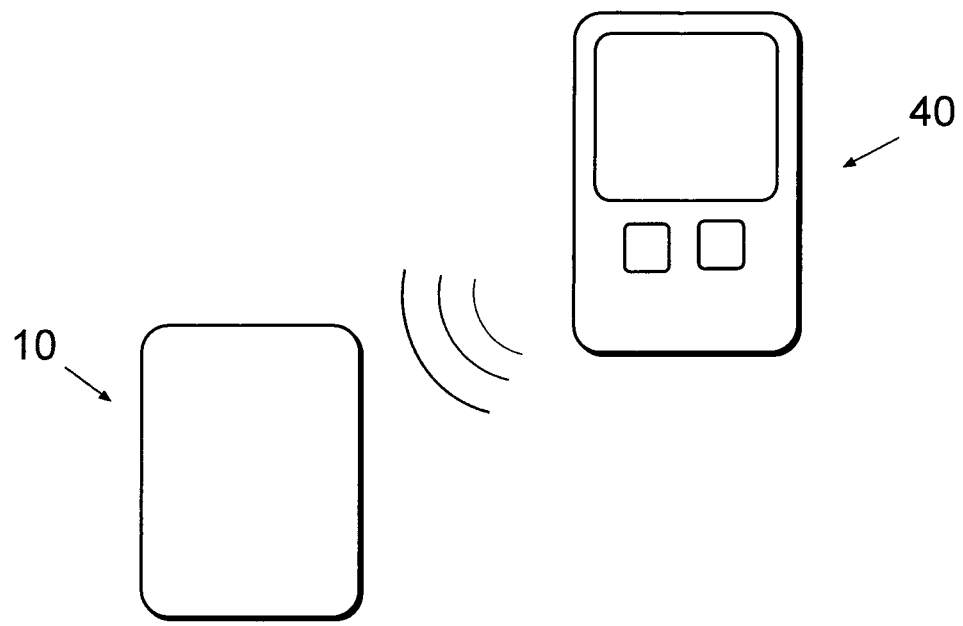
FIGS. 1a-e are schematic diagrams of exemplary single-part dispensing unit and a two-part dispensing unit, with and without operational buttons and a remote control unit.
Figure 1B:
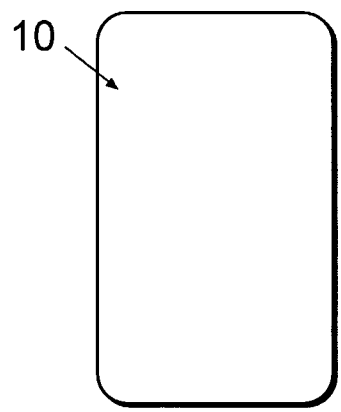
Figure 1C:
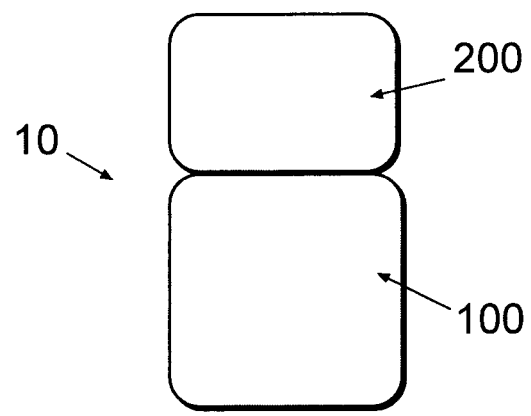

Referring to FIG. 1a, a schematic diagram of a fluid delivery device that includes a dispensing unit 10 and a remote control unit 40 is shown. In some embodiments, the dispensing unit 10 may be a single part unit (as depicted in FIG. 1b) or a two-part unit (as depicted in FIG. 1c). In embodiments in which a two-part unit is used, the dispensing unit 10 includes a first portion (e.g., a reusable part) 100 and a second portion (e.g., a disposable part) 200. The dispensing unit 10 may be implemented using different dispensing mechanisms, such as a syringe-type reservoir with a propelling plunger, peristaltic positive displacement pumps, etc. In some embodiments, the dispensing unit 10 can be secured (e.g., adhered) to a patient's body. In some embodiments, the patch unit includes a dispensing apparatus for delivering therapeutic fluids (e.g., insulin) and a sensing apparatus for sensing analytes (e.g., glucose) within the body.

Figure 1D:
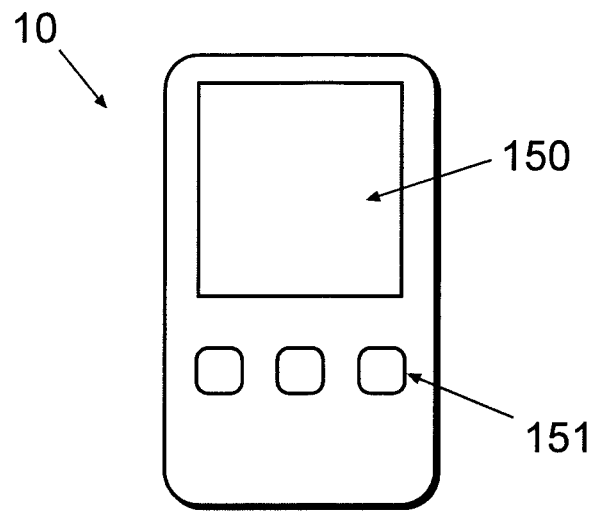
Figure 1E:
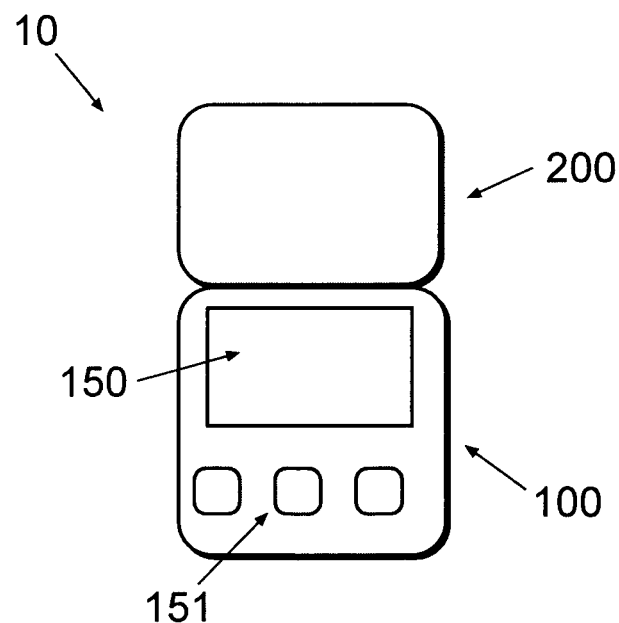

Infusion programming, data transferring and control of the dispensing unit can be performed using a remote control unit 40 which may be implemented as a PDA (Personal Digital Assistant), watch, cellular phone or the like, and/or by using operational buttons 151 disposed on the dispensing unit 10. The remote control unit 40 is configured to establish a unidirectional or bidirectional communication link with the dispensing unit 10. As shown in FIG. 1d, in some embodiments, the dispensing unit 10 includes a display 150 and operational buttons 151 for controlling and programming the dispensing unit 10. In some embodiments, the two-part dispensing unit 10 (such as, for example, the two-part unit shown in FIG. 1e), includes a reusable part 100 and disposable part 200. The reusable part 100 of such embodiments includes a user interface (e.g., a display 150 and operational buttons 151). The configurations of the dispensing units shown in FIGS. 1a-e are also described, for example, in previously filed U.S. Provisional Applications Nos. 60/963,148 and 61/004,019, the contents of which are hereby incorporated by reference in their entireties.

Figure 2A:
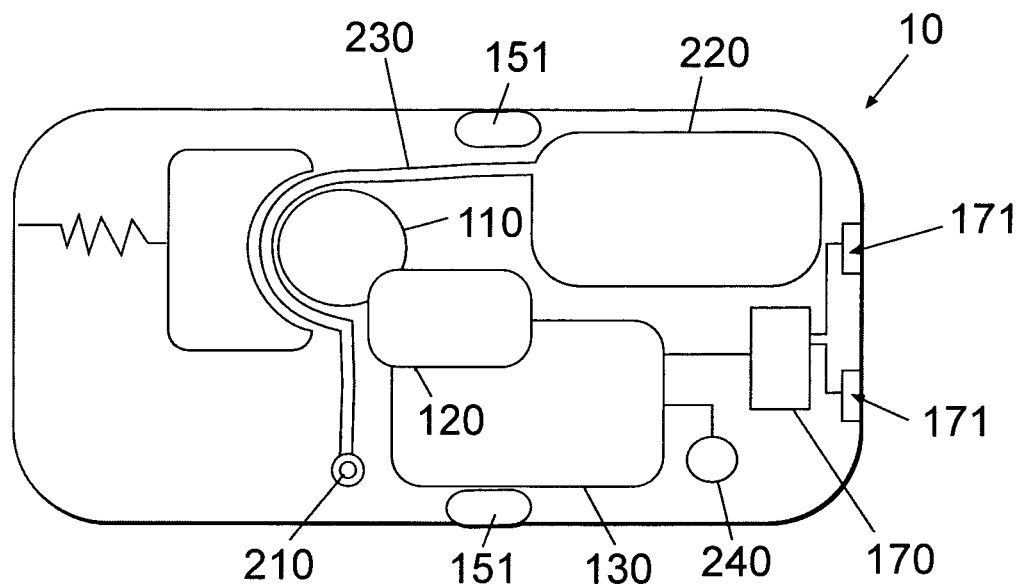
FIGS. 2a-c are schematic diagrams and views of a single-part dispensing unit and a two-part dispensing unit (2b) employing a peristaltic pumping mechanism.
Figure 2B:
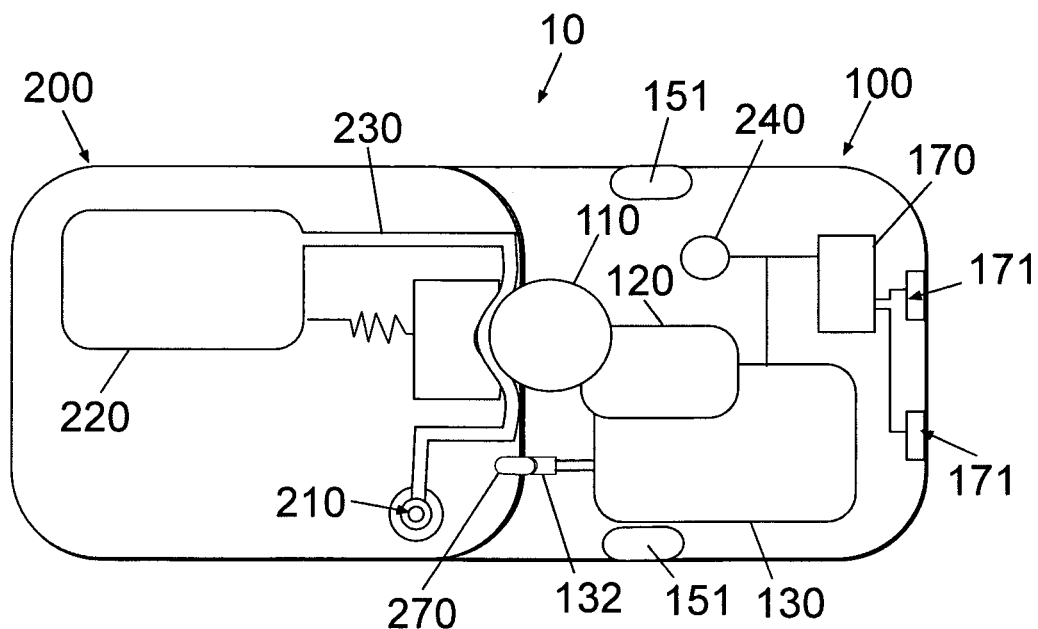
Figure 2C:
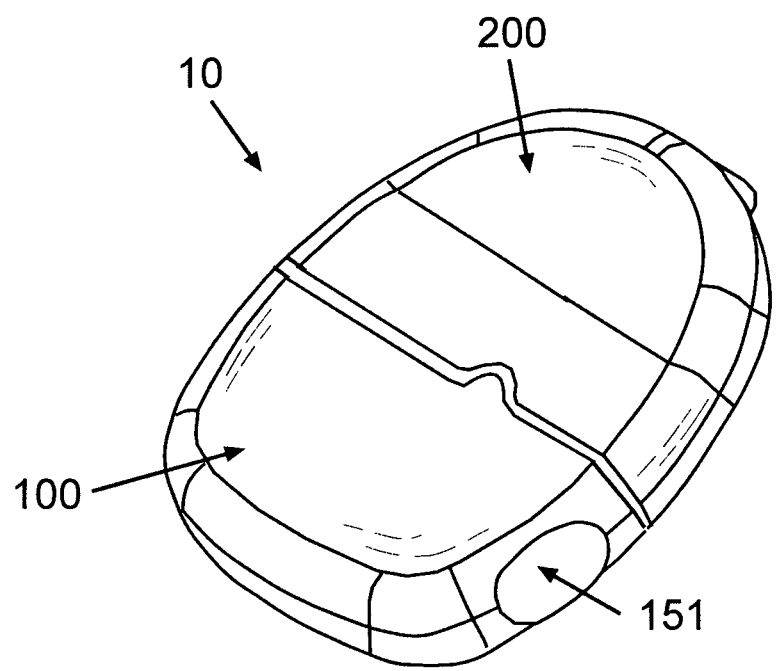

FIGS. 2a, 2b and 2c are schematic diagrams and views of an exemplary dispensing unit 10 employing a peristaltic pumping mechanism for dispensing therapeutic fluid to a user's body.

Referring to FIG. 2a, a schematic diagram of a single-part dispensing unit 10 is shown. The fluid is delivered from a reservoir 220 to an outlet port 210 through peristaltic squeezing of a tube 230 by a rotary wheel 110. A description of an exemplary positive displacement pump that may be used in conjunction with the dispensing unit 10 of FIG. 2a is provided, for example, in previously filed U.S. patent application Ser. No. 11/397,115, the content of which is hereby incorporated by reference in its entirety. A driving mechanism 120, including gears and a motor, e.g. a Stepper motor, DC motor, SMA actuator and the like, can be used for rotating the rotary wheel 110. The driving mechanism 120 is controlled by a controller module (e.g., a module including electronic components, such as CPU) residing in the dispensing unit 10. Such electronic components may include, in some embodiments, a processor-based device and a transceiver (transmitter/receiver unit). The electronic components of the controller module are schematically designated by a reference numeral 130. A rechargeable energy storage unit (e.g., one or more batteries, including one or more rechargeable batteries) 240 and electrical coupling connectors (also refer-to as "connectors" or electrical connectors) 171 (e.g., a DC socket) that enable electrical connection to an outer power source (such as transformer connected to a home power or a plug to a car DC socket) are also provided. The connectors are connected to a charging mechanism (which may include a rectifier and/or a voltage stabilizer to transfer the power required for charging the rechargeable energy storage unit 240 without overheating or overcharging it).

Infusion programming may be performed through the remote control unit (not shown in FIG. 2a) and/or by operating buttons 151 disposed on the dispensing unit 10.

Referring to FIG. 2b, a schematic diagram of a two-part dispensing unit 10 that includes a reusable part 100 and a disposable part 200 is shown. The reusable part 100 includes a positive displacement pump provided with a rotary wheel 110, a driving mechanism 120, electronic components 130 (implementing, for example, an electronic controller to control the pump) and a rechargeable energy storage unit 240. The disposable part 200 includes a reservoir 220, a delivery tube 230 and an outlet port 210. Further details regarding an arrangement such as this are provided, for example, in previously filed U.S. patent application Ser. No. 11/397,115, the content of which is hereby incorporated by reference in its entirety. Dispensing of therapeutic fluid is achieved when the dispensing unit 10 is assembled by mechanically connecting the reusable part 100 and disposable part 200. An, indicator indicating that the two parts are in proper connection is provided by a socket 132, located in the reusable part 100, and a plug 270, located in the disposable part 200. When the dispensing unit 10 is properly assembled the plug 270 and the socket 132 are connected so as to establish a closed electrical circuit that causes the indicator to be powered and thus to indicate the connection status of the two parts. In some embodiments, the socket 132 may also function as a connector to an external power source. Consequently, the rechargeable battery/batteries (of the energy storage unit 240) can be recharged when the dispensing unit is disassembled to thus enable the establishing an electrical connection between the energy storage unit 240 and an electrical outlet. In these embodiments, there are no exposed connectors when the dispensing unit 10 is assembled, thus preventing the occurrences of short circuits. Alternatively, in some embodiments the socket is lockated in the reusable part and the plug is located in the disposable part.

FIG. 2c is an isometric view of an exemplary two-part dispensing unit 10. As shown, the reusable part 100 and the disposable part 200 are connected, thus constituting the dispensing unit 10 in its assembled state. Fluid delivery programming can be performed using a remote control unit (not shown) or by operational buttons 151 located on the reusable part 100 housing.

Figure 3A:
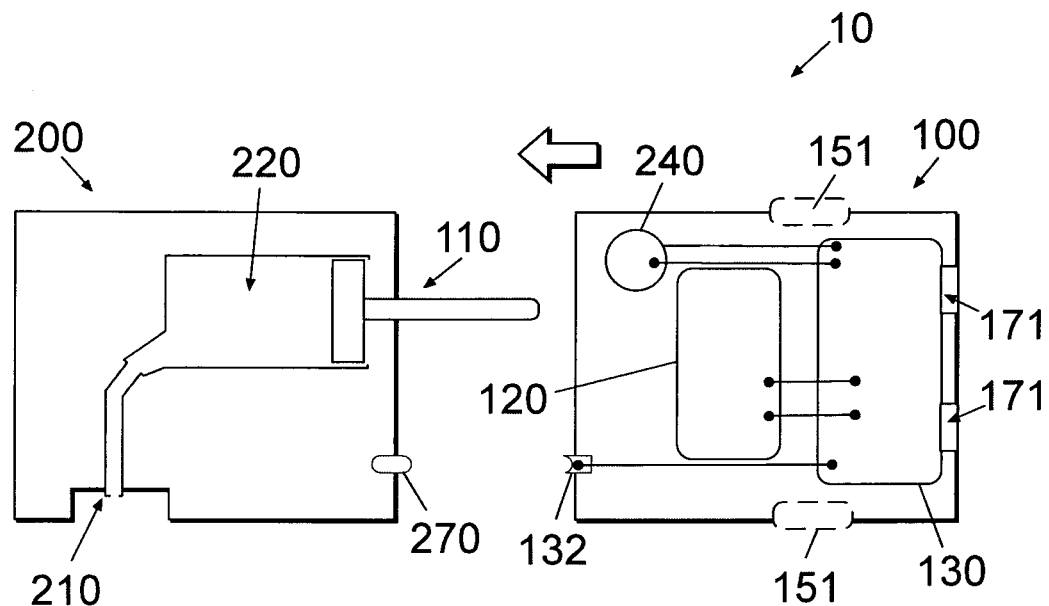
FIGS. 3a-b are schematic diagrams of exemplary single-part dispensing unit and a two-part dispensing unit employing a syringe-piston pumping mechanism.
Figure 3B:
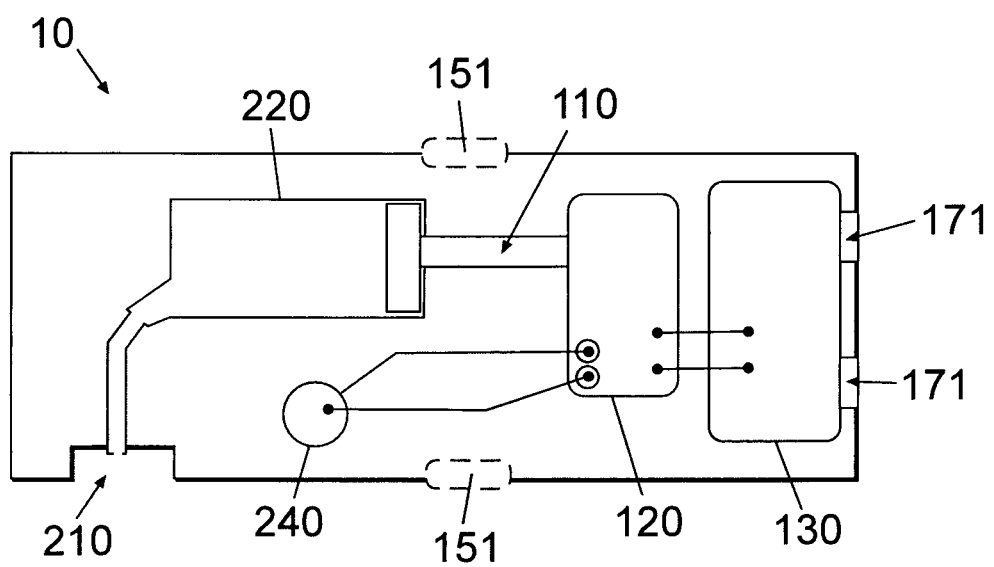

FIGS. 3a and 3b are schematic diagrams of exemplary embodiments of a dispensing unit 10 employing a piston/plunger pumping mechanism. A description of embodiments of a dispensing unit employing this type of pumping mechanism is disclosed, for example, in previously filed U.S. provisional application No. 60/928,751, filed on the May 11, 2007, the content of which is hereby incorporated by reference in its entirety.

Referring to FIG. 3a, as shown, in some embodiments, the dispensing unit 10 is a two-part dispensing unit having a reusable part 100 and a disposable part 200.

The disposable part 200 includes: a reservoir 220 coupled to a plunger 110 and an outlet port 210. In some embodiments, the plunger 110 may be located in the reusable part 100 or may extend over both parts such that a section of the plunger 110 is located in the reusable part 100 and another section of the plunger 110 is located in the disposable part 200. As further shown, a plug 270 is also provided to indicate whether the disposable part 200 is connected to the reusable part 100 such that when the reusable part 100 and the disposable part 200 are mechanically secured to each other an indication circuit other an indication circuit connected to a socket 132 located in the reusable part 100 is electrically closed thus causing the indication circuit to be activated The reusable part 100 includes: a driving mechanism 120, which includes a motor (e.g., Stepper motor, DC motor, SMA actuator and the like), and gears to displace the plunger 110. The driving mechanism 120 is controlled by electronic controls 130 which may include a controller, processor and transceiver (not shown). Infusion programming can be carried out by a remote control unit (not shown) and/or by one or more operating buttons 151 disposed at the exterior surface of the dispensing unit 10. At least one rechargeable battery 240 disposed in the reusable part 100 provides energy to at least some of the modules/components of the reusable part 100 such as the motor. The charging current to recharge the rechargeable battery 240 is delivered via connectors 171. Recharging operations may be controlled by the dispensing unit electronic controls 130.

Referring to FIG. 3b, a single-part dispensing unit 10 is shown that includes a reservoir 220 coupled to a plunger 110 and an outlet port 210. The dispensing unit 10 further includes a driving mechanism 120, which includes a motor (e.g., Stepper motor, DC motor, SMA actuator or the like), and gears to displace the plunger 110. The driving mechanism 120 is controlled by electronic controls 130 which may include a controller, processor and transceiver (not shown). Infusion programming can be carried out by a remote control unit (not shown) and/or by one or more operating buttons 151 disposed at the exterior portion of the dispensing unit 10. At least one rechargeable battery 240 disposed in the reusable part 100 provides energy to at least some of the modules/components of the reusable part 100 such as the motor. The charging current to recharge the rechargeable battery 240 is delivered from a charging unit via connectors 171. Recharging operations may be controlled by the dispensing unit electronic controls 130.

Figure 4:
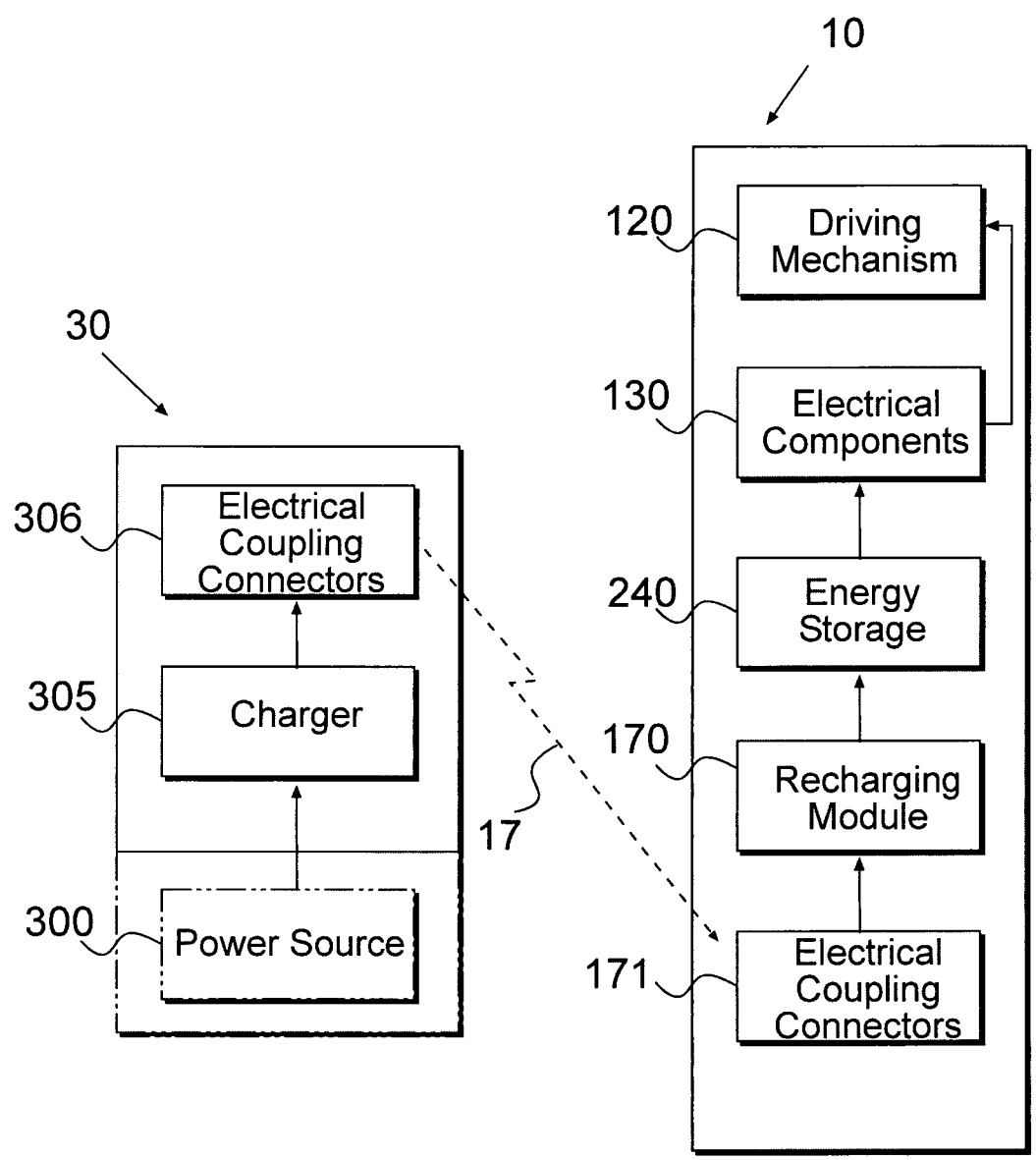
FIG. 4 are block diagrams depicting an exemplary energy supply from a recharging unit to a dispensing unit's electrical components.

Referring to FIG. 4, schematic block diagrams of an exemplary recharging unit 30 and an exemplary dispensing unit 10 are shown. The recharging unit 30 includes a charger 305 that directs charging current 17 to the dispensing unit recharging module 170 when the electrical coupling connectors 171 and 306 of the dispensing unit 10 and the recharging unit 30, respectively, are coupled to each other. The set of electrical connections 306 (e.g., DC connector, USB plug, coil, etc.) is generally included in the recharging unit 30 while the other set of electrical connections 171 is included in the dispensing unit 10. The dispensing unit recharging module 170 directs charging current to the rechargeable energy storage (e.g., battery) 240. Thus, the battery 240 can be charged while embedded in the dispensing unit 10 (i.e., the energy storage 240 may be an internal battery that does not have to be removed from the housing of the dispensing unit 10). The battery 240 supplies energy to components of the dispensing unit 10 such as the driving mechanism, processor, transceiver, etc. The charging current 17 may be transferred to the dispensing unit 10 wirelessly, e.g. by induction, RF transmission, etc., or it may be transferred to the dispensing unit by wires.

The recharging unit 30 can include an internal power source 300 (e.g., solar cell, one or more batteries, etc.), and/or can be connected to an external power source such as a power line, a car DC socket, or to other device power outlets such as a USB host.

In some embodiments, the electrical communication between the dispensing unit 10 and the recharging unit 30 (e.g., when the recharging unit 30 is directing charging energy to the dispensing unit) may be detected by measurement of voltage or current at the electrical connectors 171 and/or 306 of the dispensing unit 10 or recharging unit 30, respectively. In such embodiments, additional components may be required, e.g., a processor and/or digital logical circuitry for use, for example, with an analog to digital (A/D) converter.

Figure 5A:
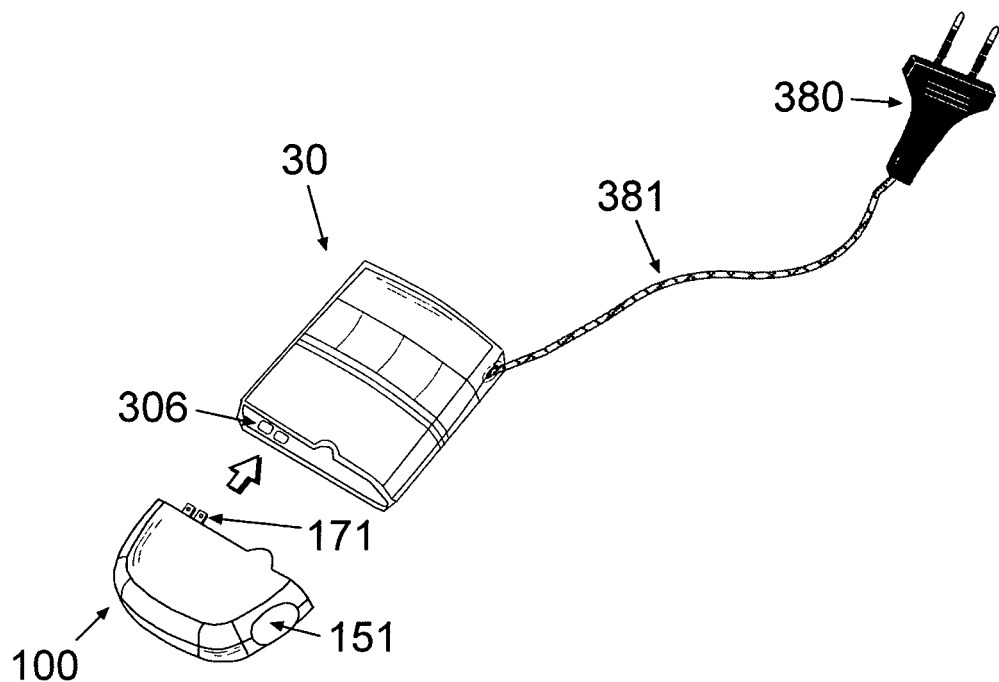
FIG. 5a is a perspective view of an exemplary recharging unit connectable to a rechargeable reusable part.

Referring to FIG. 5a, a perspective view of an exemplary rechargeable reusable part 100 connectable to a recharging unit 30 to charge the rechargeable reusable part is shown. The recharging unit 30 includes connectors 306, power cords 381 and plug 380 to connect the recharging unit 30 to an external power source. The connectors 306 are mechanically connectable to the reusable part electrical connectors 171 to provide electrical connection between the recharging unit 30 and the reusable part 100. Plug 380 enables delivery of power current to the recharging unit 30 from a household power wiring.

Figure 5B:
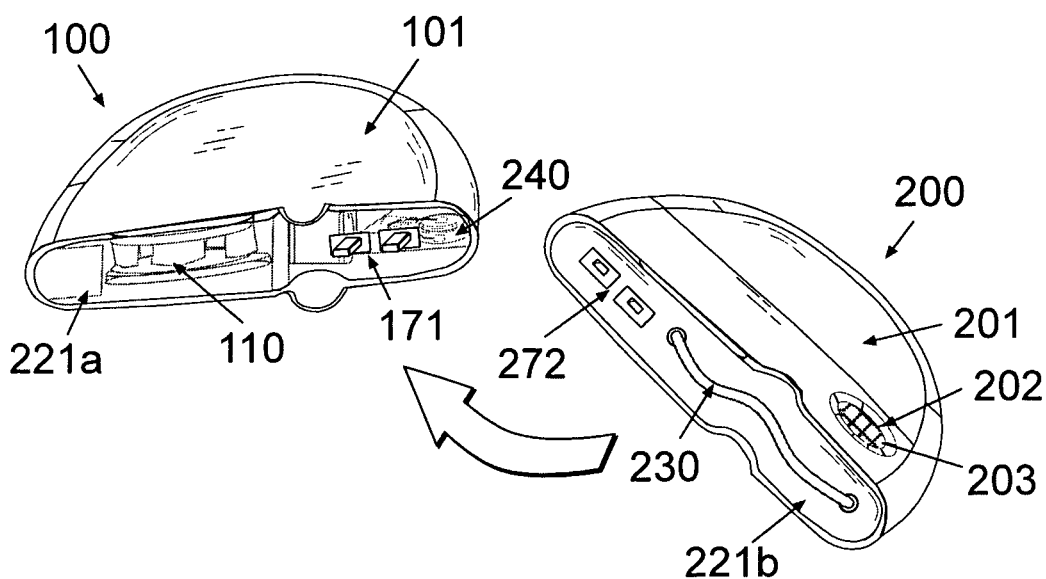
FIG. 5b is a perspective view of an exemplary two-part rechargeable dispensing unit.

FIG. 5b is a perspective view of an exemplary two-part dispensing unit that includes a rechargeable reusable part 100 and a disposable part 200. Housings 101 and 201 of the reusable part 100 and the disposable part 200, respectively, form, in some embodiments, a water tight seal using elastic seals 221a and 221b. Mechanical coupling of the rotary wheel 110 and the tube 230 enables peristaltic pumping. A vent 202, covered by a selectively permeable membrane (e.g. Gore-Tex®) 203, is provided to, for example, balance the pressures between the interior and the exterior of the disposable part 200. A description of an exemplary water tight dispensing pump is provided, for example, in previously filed Provisional Application No. 60/961,382, entitled "Vented Dispensing Device and Method," the content of which is hereby incorporated by reference in its entirety. While FIG. 5b shows an embodiment of a dispensing unit implemented with a peristaltic pumping mechanism, in some embodiments, the dispensing unit may include other types of pumping mechanisms, including, for example, mechanisms with syringe-based reservoirs and propelling plungers, etc. Furthermore, in some embodiments, the vent, such as the vent 202 of FIG. 5b, may be located in other parts of the dispensing unit, including, for example, the reusable part of the dispensing unit. In some embodiments, both the reusable and disposable parts of a dispensing unit may include vents to facilitate the dispensation functionality of the unit. Electrical connectors 171 protrude from the sealed housing 101 to enable electrical connection to the recharging unit's connectors. A socket 272 is provided in the disposable part housing 201 that is connectable to the connectors 171 of the reusable part 100 when the two parts of the dispensing unit 10 are attached. The socket 272 may include (or be coupled to) an indication mechanism to indicate when the two parts (i.e., the reusable part 100 and the disposable part 200) are attached.

Figure 5C:
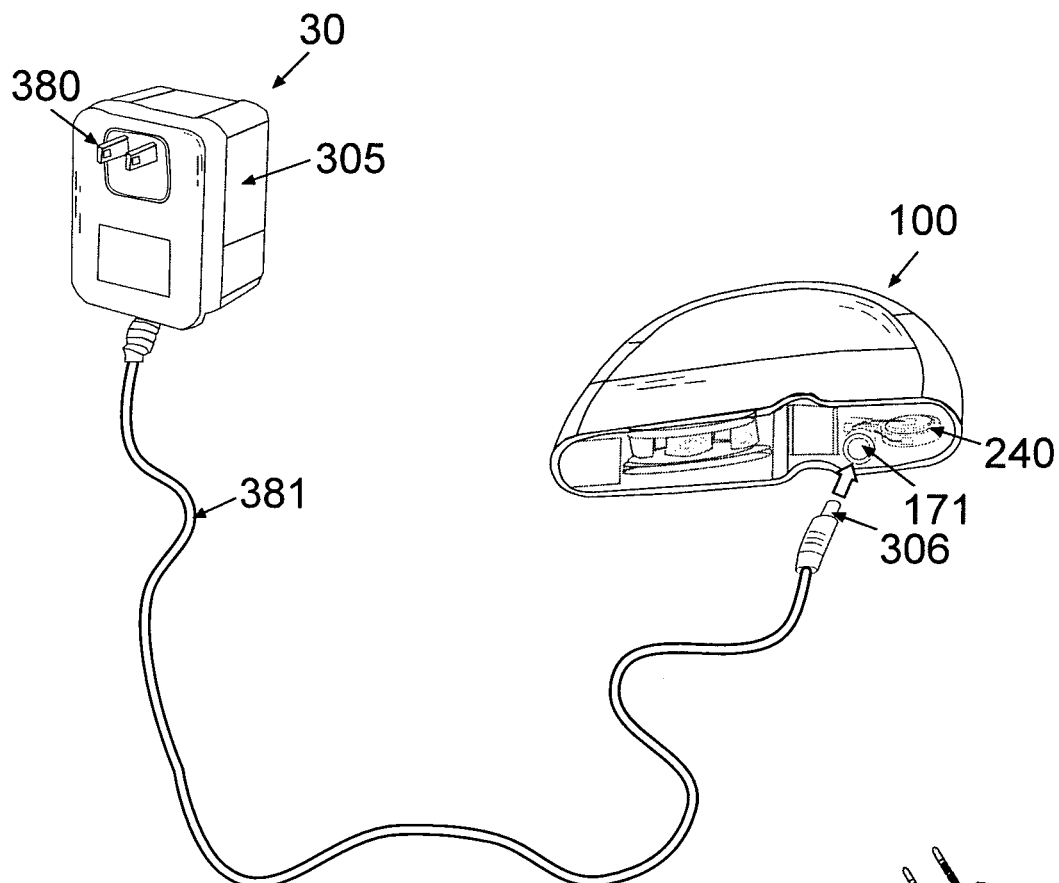
FIG. 5c is a perspective view of an exemplary recharging unit with AC/DC transformer connectable to a rechargeable reusable part of a dispensing unit.

Referring to FIG. 5c, a perspective view of an exemplary rechargeable reusable part 100 connectable to a charger 30 that includes a plug 380, a charger 305 (e.g., AC/DC transformer), power cords 381 and a connector 306 (e.g., a DC plug) is shown. The reusable part 100 of the dispensing unit comprises a connector 171 (e.g., DC socket) connectable to the connector 306 (DC plug) to recharge the rechargeable energy storage (battery) 240.

Figure 6:
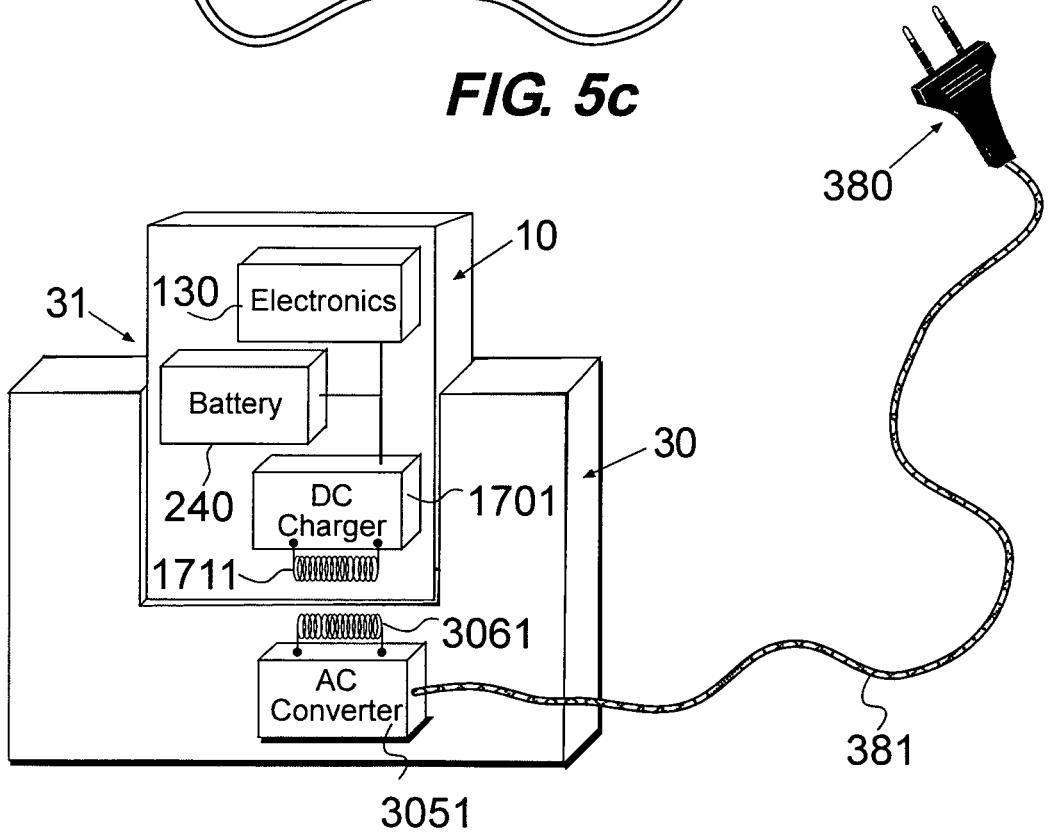
FIG. 6 is a schematic diagram of an exemplary magnetic induction energy transfer mechanism from a recharging unit to a rechargeable dispensing unit.

Referring to FIG. 6, a schematic diagram of an exemplary rechargeable dispensing unit 10 coupled to a recharging unit 30 having a magnetically inductive energy transfer mechanism is shown. The recharging unit 30 includes a primary winding 3061, an AC converter 3051 (functionally equivalent, for example, to the charger 305 shown in FIG. 4), power cords 381 and a plug 380. The recess 31 located in the recharging unit 30 is configured to be spatially aligned with the dispensing unit 10 such that when the dispensing unit 10 is received within the recess 31 the two windings 3061 and 1711 are spatially positioned as a two-part transformer. Energy (e.g., current) supplied through the plug 380 is converted by the AC converter 3051 to a required AC voltage/current level power (in terms of frequency, amplitude, etc.) and transferred by primary winding 3061 to the secondary winding 1711. Descriptions of separable transformers are provided, for example, in U.S. Pat. Nos. 3,418,552, 3,840,795, 3,939,391, 4,374,354, 4,942,352, 5,157,319 and 5,680,028, the contents of all of which are hereby incorporated by reference in their entireties. The charger 1701 may include a rectifier, which converts the AC voltage/current received by the secondary winding 1711 to a DC power level (i.e., DC voltage/current levels) required to charge the battery 240. In some embodiments, the charger 1701 also regulates the charging of the battery 240 to prevent overheating or overcharging. A description of such charger regulating functionality is provided, for example, in U.S. Pat. No. 4,065,712, the content of which is hereby incorporated by reference in its entirety. In some embodiments, the charging process is performed in accordance with the requirements (e.g., safety, compatibility, insulation) of such standards as the standards for medical devices EN-IEC 60601 or EN-IEC 60602.

With continued reference to FIG. 6, the primary and secondary windings 3061 and 1701 constitute the electrical connection in a manner similar, for example, to the connection constituted by the connectors 306 and 171 shown in FIG. 4. The AC converter and DC charger shown in FIG. 6 are functionally analogous to the charger 305 and the recharging module 170, respectively, shown in FIG. 4.

Figure 7A:
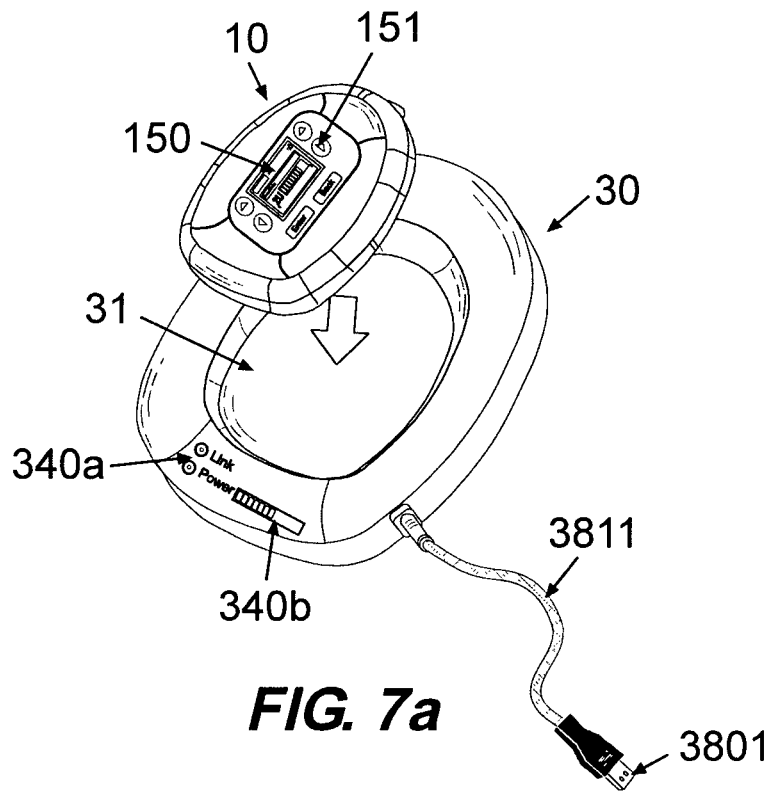
FIG. 7a is a perspective view of an exemplary inductively recharging unit connectable to a rechargeable dispensing unit.

Referring to FIG. 7a, a perspective view of an exemplary recharging unit 30 to transfer power to a dispensing unit 10 via an inductive energy transfer implementation is shown. The recharging unit 30 includes a recharging recess 31 configured to receive the dispensing unit 10 (a single part dispensing unit or an assembled two-part dispensing unit). The recharging unit 30 further includes a USB plug 3801 and a USB cable 3811 to connect it to a USB host (e.g., a personal computer). The USB host supplies power to the recharging unit 30 when connected. Recharge status indication devices, such as, for example, LEDs 340a and monitor 340b, are provided to indicate the connection and recharging status. In some embodiments, the status indication device 340a includes two LEDs that respectively indicate the connection status between the recharging unit 30 and the reusable part 100 (denoted as "link") and the status for the USB host connection (denoted as "power"). In some embodiments, the indication device 340b includes a status bar to indicate the charging progress. The dispensing unit 10 also includes operating buttons 151 to enable receipt of user inputs, and a display 150 to provide indications and outputs.

Figure 7B:
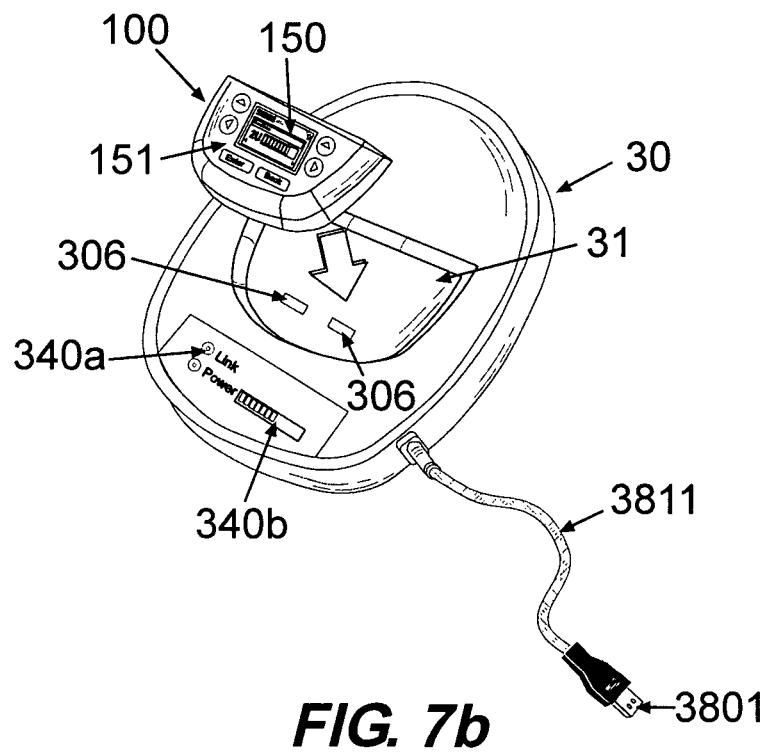
FIGS. 7b-c are perspective views of an exemplary recharging unit connectable to an exemplary rechargeable reusable part of a dispensing unit.
Figure 7C:
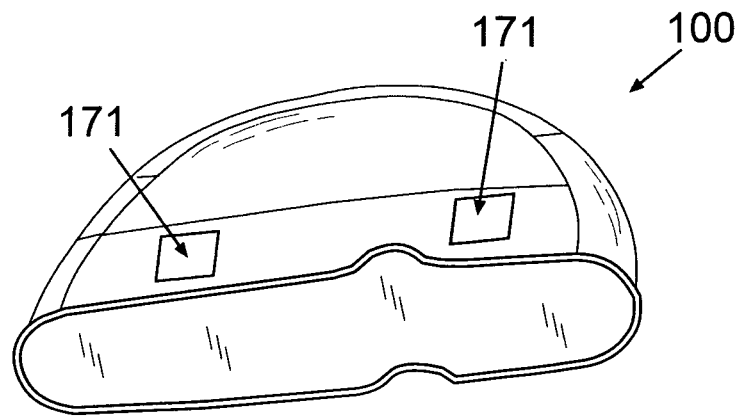

Referring to FIG. 7b, a perspective view of another exemplary recharging unit 30 configured to house a reusable part 100 of a dispensing unit when detached from a disposable part is shown. Two pairs of electrical connectors, namely, one pair of connectors 306 located on the recharging unit 30 and another pair of connectors located on the bottom side of the reusable part 100 (designated as numeral 171, as shown in FIG. 7c) provide an electrical connection between the reusable part 100 and the recharging unit 30 when the reusable part 100 is placed in the recharging recess 31 of the recharging unit 30.

Figure 8:
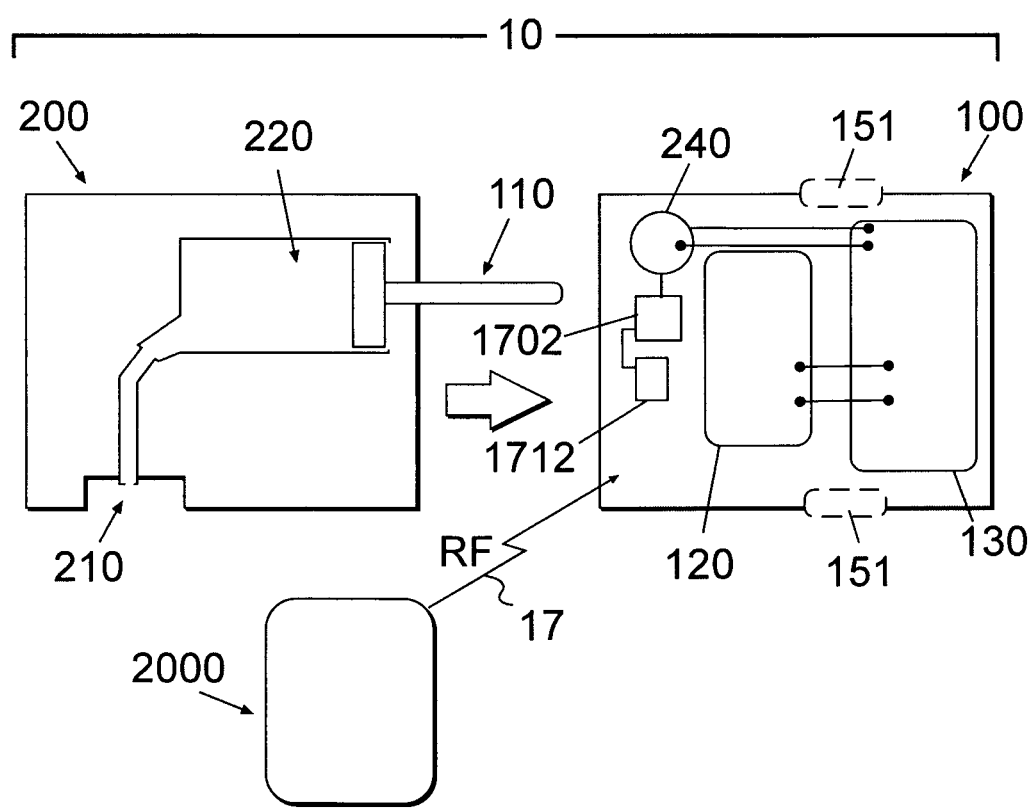
FIG. 8 is a schematic diagram of an exemplary rechargeable dispensing unit with an RF recharging mechanism.

Referring to FIG. 8, a schematic diagram of an exemplary rechargeable dispensing unit 10 that includes a wireless recharging circuit 1702, such as commercially available Powercast™ recharging circuit, and an antenna 1712, is shown. RF waves 17 are received by the antenna 1712 and are converted to DC power by the wireless recharging circuit 1702. The converted power is used to charge a rechargeable battery 240. In this embodiment, the wireless recharging circuit 1702 and antenna 1712 are functionally analogous to the recharging module 170 and electrical coupling connectors 171 shown in FIG. 4.

Figure 9:
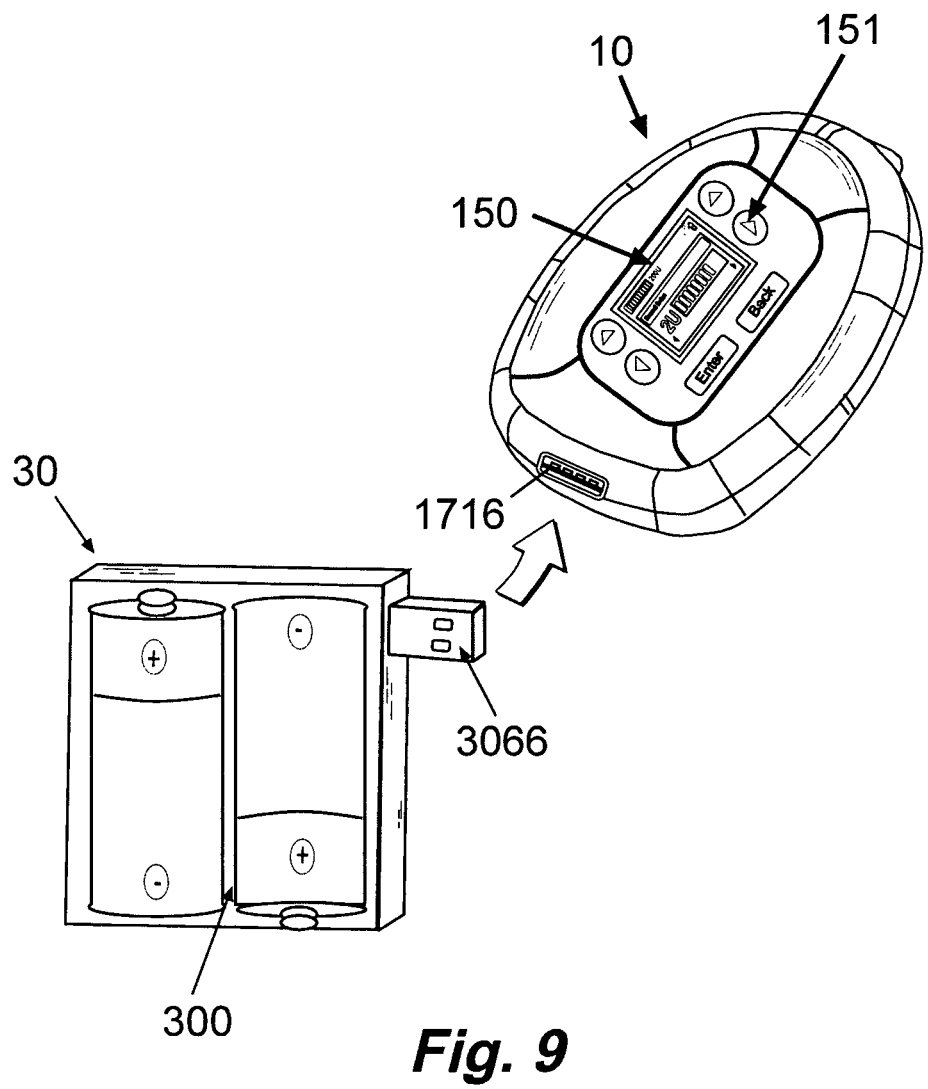
FIG. 9 is a perspective view of an exemplary portable recharging unit connectable to a rechargeable dispensing unit.

Referring to FIG. 9, a perspective view of an exemplary portable recharging unit 30 is shown. The portable recharging unit 30 includes:
  An internal power source 300 (e.g., two batteries), thus avoiding the need for charging from stationary power source (e.g., home power socket), and enabling the dispensing unit 10 to be recharged while being carried.
  A USB connector 3066 connectable to a USB port 1716 located in the dispensing unit 10 (in a two-part dispensing unit, the USB port 1716 may be located on the reusable part of the unit). When electrically coupled, the recharging unit power source 300 supplies the energy to the dispensing unit 10 and thus the dispensing unit can be recharged without movement or traveling limitations.

In some embodiments, the dispensing unit 10 can be recharged by the portable recharging unit 30 during operation, thus avoiding treatment interruption.

Figure 10:
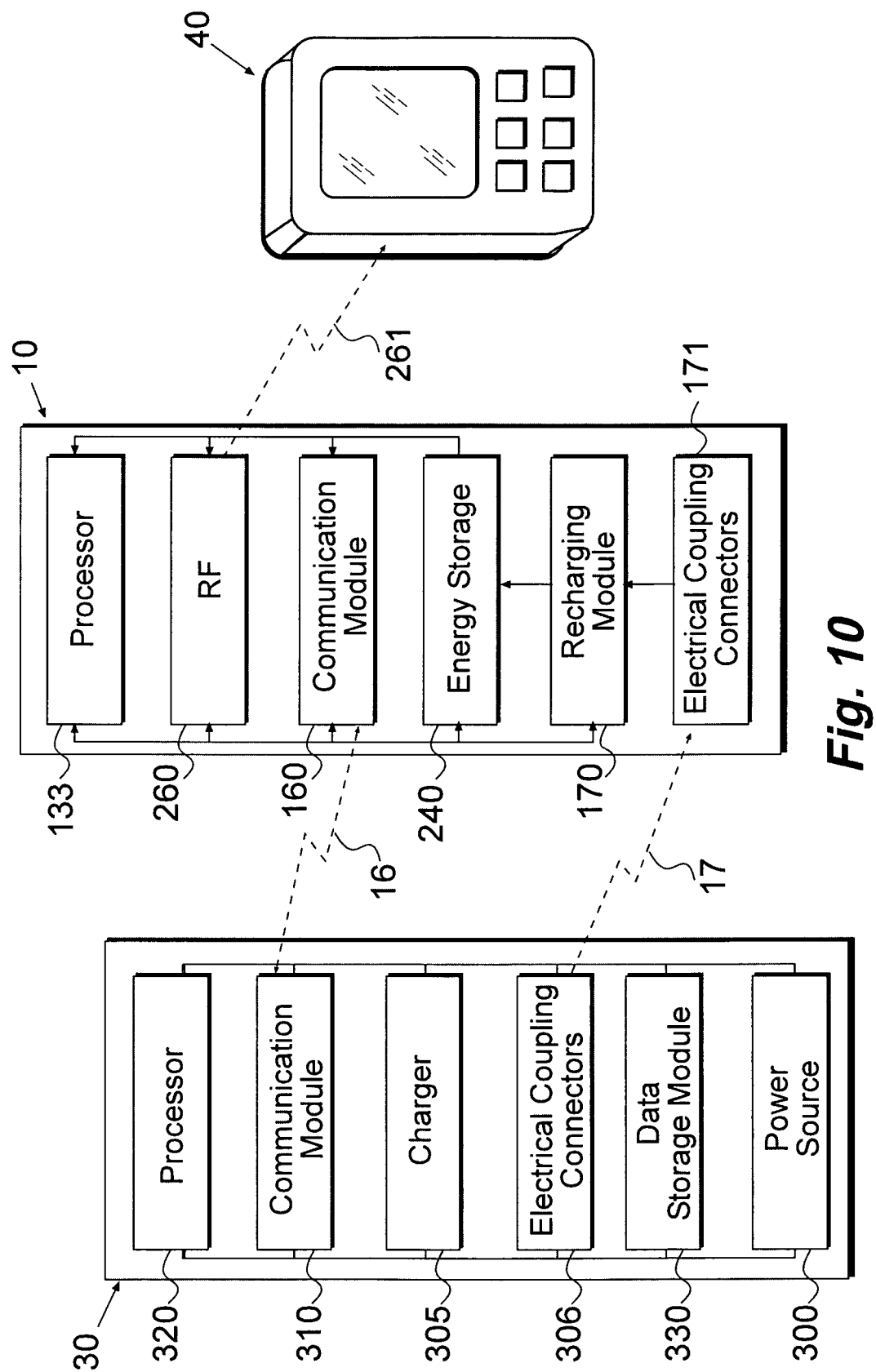
FIG. 10 is a block diagram of an exemplary energy and data transfer implementation between a recharging unit and a dispensing unit with a remote control.

Referring to FIG. 10, a block diagram of a system that enables energy and data transfer between a dispensing unit 10 in communication with a remote control unit 40 and a recharging unit 30 is shown. The recharging unit includes a processor 320, a communication module 310 and data storage module 330. A communication link 16 established between the dispensing unit 10 and the recharging unit 30 enables, for example, the backup of data stored in the dispensing unit 10, and further enables updating of data stored in the dispensing unit (e.g., user related data, including infusion profiles, software or firmware updates, etc.). Data stored in the data storage module 330 of the recharging unit 30 is processed by the processor 320 and transferred through the recharging unit's communication module 310 to the dispensing unit's communication module 160, and vice versa. The dispensing unit 10 also includes an RF transceiver 260 to communicate, e.g., through an established RF communications link 261, with the remote control unit 40. In some embodiments, communications links 16 and/or 261 other than the RF communication links may be used. For example magnetic links, infrared (IR) communication links, wired communication links, etc., may be used in addition to or instead of RF links. The communications links 16 and/or 261 may be unidirectional or bi-directional.

Figure 11A:
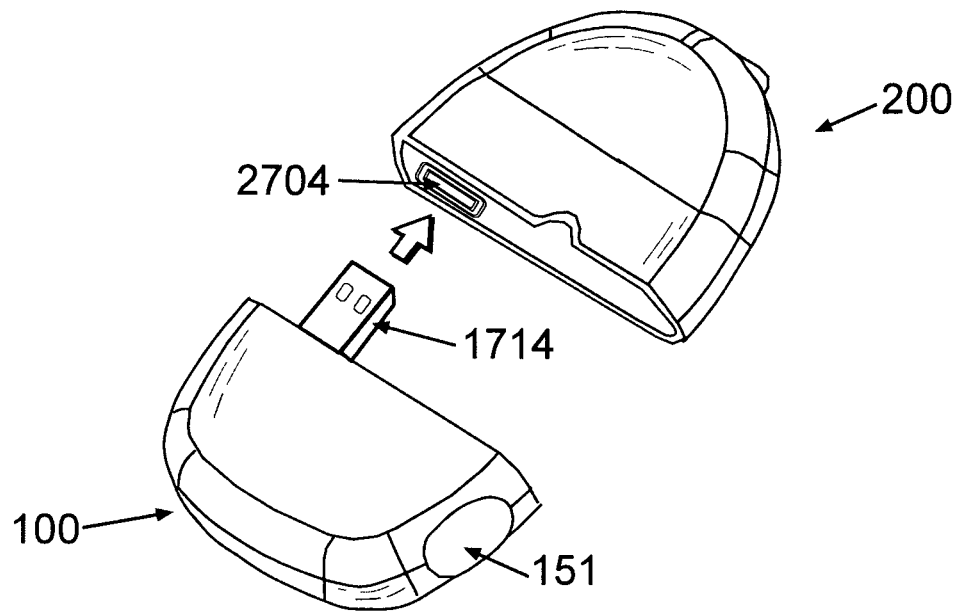
FIGS. 11a-b are perspective views of exemplary rechargeable dispensing units with USB plugs.

Referring to FIG. 11a, a perspective view of an exemplary system that includes a reusable part 100 with a USB plug 1714 to transfer data and energy is shown. When the reusable part 100 is coupled to a disposable part 200 to form an assembled dispensing unit, the USB plug 1714 is mechanically connected to a USB socket 2704. An indication device (not shown) may provide an indication as to whether the USB socket 2704 and plug 1714 are mechanically connected. The reusable part 100 is connectable, e.g., via a USB plug to a USB host (not shown in the figure). When connected to the USB host, energy and/or data can be transferred between the reusable part and the USB host. The data so transferred may have been, or may subsequently be, stored, edited and/or managed.

Figure 11B:
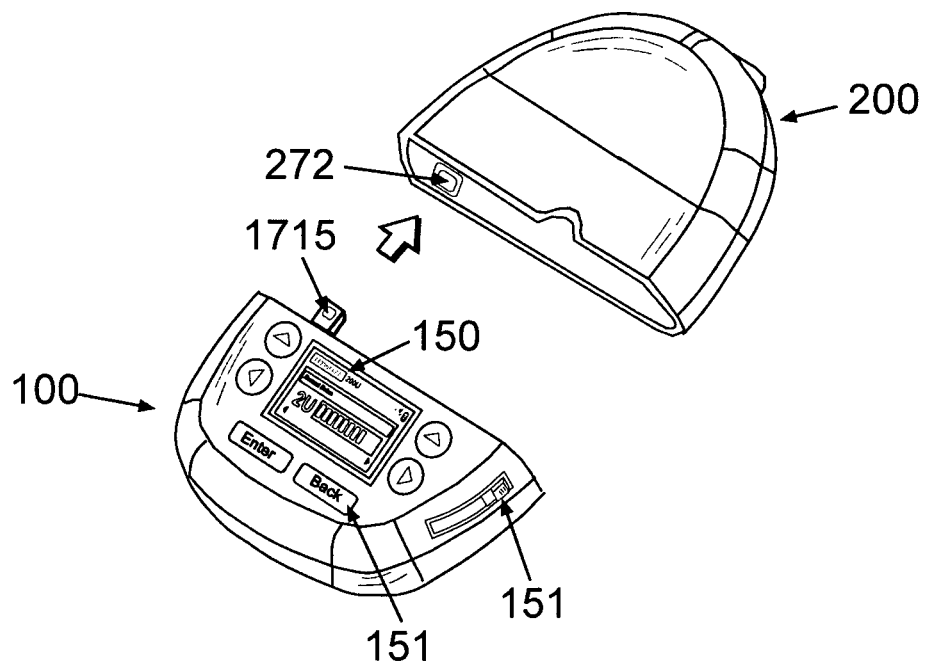

Referring to FIG. 11b, a perspective view of another exemplary system that includes a reusable part 100 with a mini-USB jack 1715 (instead of standard USB plug "A" type) is shown. The mini-USB plug 1715 is smaller than the standard USB plug "A", and thus can be applied more discreetly in a dispensing unit 10 (i.e., the mini-USB jack is less conspicuous than the USB plug "A" shown in FIG. 11a). In some embodiments, the reusable part 100 can further include a display/screen 150 and operational buttons 151.

Figure 12:
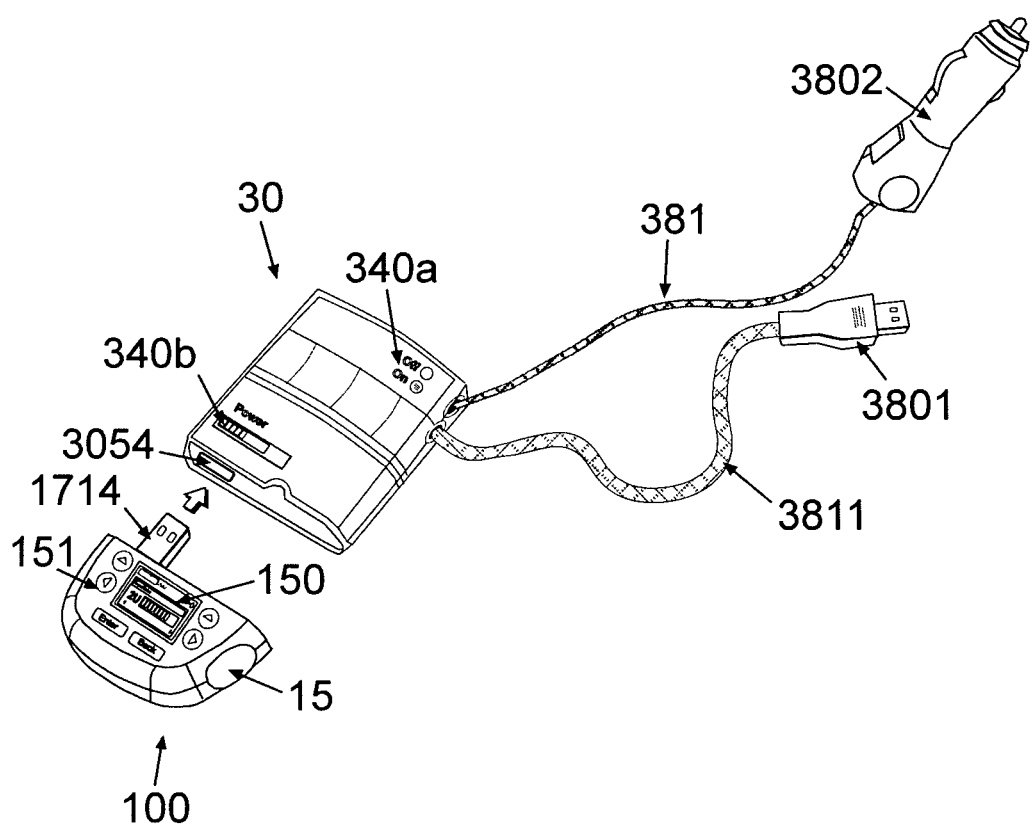
FIG. 12 is a perspective view of a rechargeable reusable part with a USB plug and a recharging unit with a USB socket.

Referring to FIG. 12, a perspective view of an exemplary system including a recharging unit 30 that can be recharged through a car's lighter plug is shown. The recharging unit 30 of FIG. 12 includes a USB socket 3054 connectable to the reusable part's USB plug 1714, a car lighter plug 3802 that may include a DC/DC converter for converting the voltage provided from a car lighter plug (usually 6 v or 12 v) to the voltage required to operate the dispensing pump (e.g., 5 v) or to be stored in an energy storage cell (e.g., one or more rechargeable batteries) disposed in the reusable unit 10. The recharging unit 30 also includes a power cord 381, a USB cable 3811 and a USB plug 3801 to communicate with a USB host (not shown). The car lighter plug 3802 can provide power to the dispensing unit 10 when a USB connection to a USB host is not available. In some embodiments, the recharging unit 30 can be connected simultaneously to a USB host and to another power source.

Figure 13A:
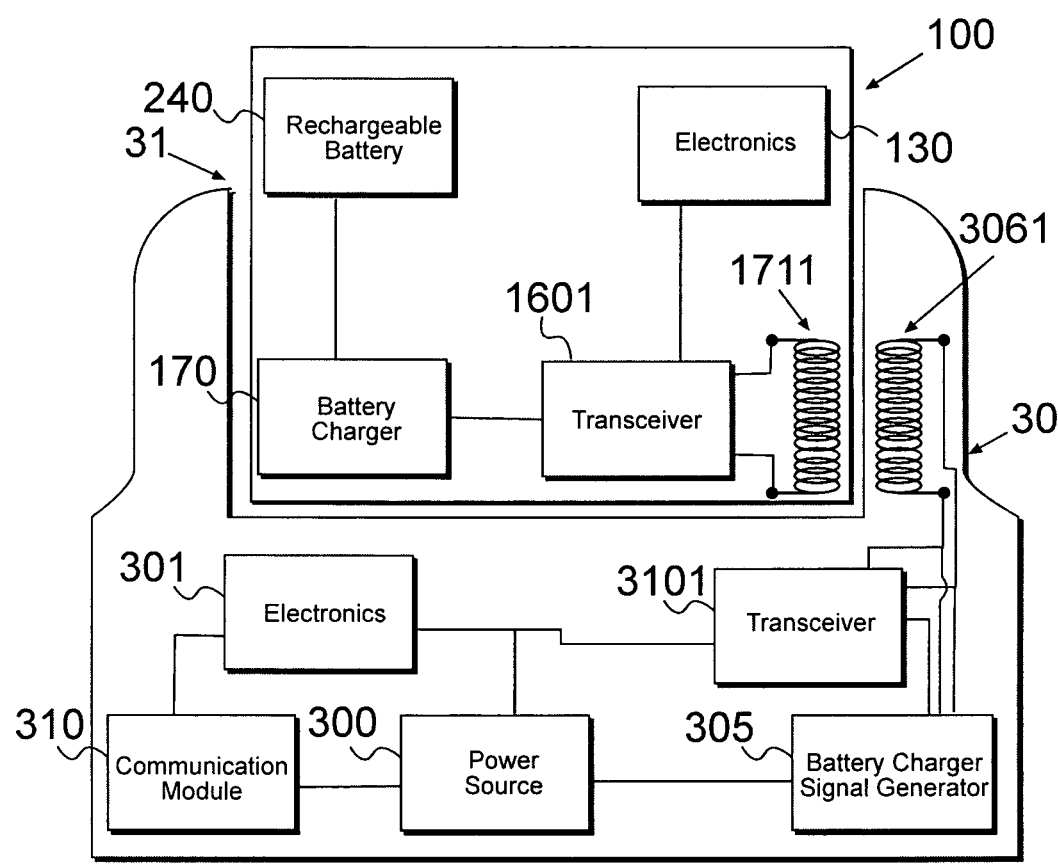
FIGS. 13a-b are schematic diagrams of exemplary energy and data transfer implementations between a recharging unit and a dispensing unit.
Figure 13B:
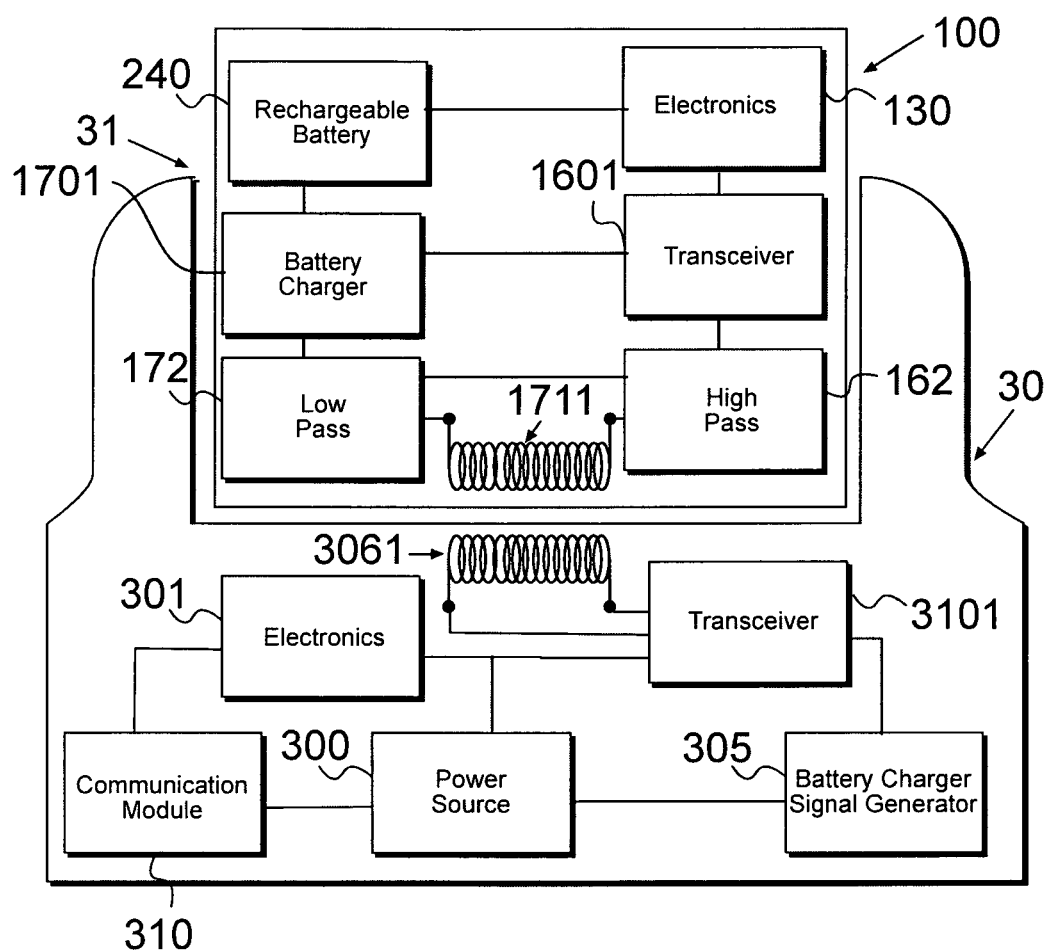

Referring to FIGS. 13a and 13b, block diagrams of exemplary systems including a recharging and data transferring unit 30 based on magnetically inductive coupling implementations are shown. Contained within each of the recharging unit 30 and a dispensing unit 10 coupled thereto are transceivers 3101 and 1601, respectively, which can simultaneously transmit and receive inductive communications signals. Full duplex operation may be implemented by echo cancellation, transmission and reception at different frequencies, time division duplex and the like. Alternatively and/or additionally, in some embodiments, separate transmitting and receiving transducers may be used.

In some embodiments, the recharging unit 30 and the dispensing unit 10 may communicate through frequency modulation of inductive fields, although other modulation methods such as amplitude or phase modulation may be employed. While charging, the distance between the recharging unit 30 and the dispensing unit 10 is, in some embodiments, less than 2 cm. This short distance reduces inductive field's radiation and noises generated by other electrical signals. As a result, use of an interference rejection circuitry may be limited or altogether not necessary.

The recharging unit transducer (primary winding) 3061 includes a coil or a ferric rod and coil wrapped around it. In some embodiments, a recess 31 defined in the recharging unit 30 is configured to hold and align the dispensing unit 10 so as to place the dispensing unit transducer 1711 in a pre-defined established position (e.g.; perpendicular, parallel and the like) relative to the recharging unit transducer 3061. The pre-defined established relative alignment of the transducers 1711 and 3061 simplifies the operation and control of the recharging and the data transfer processes because electromagnetic induction efficiency and other consequential effects (e.g., dot conversion, mutual induction, etc.) can be achieved from the relative alignment of the transducers 1711 and 3061.

The transducers 1711 and 3061 are connected to transceivers 1601 and 3101, respectively, which are controlled by electronics modules 130 and 301, respectively. The recharging unit electronics module 301 typically includes a processor, data storage device(s), and an indication device (none are shown in FIGS. 13a-b). In some embodiments, the transducers can direct the power from the recharging unit to another device (e.g. the dispensing unit, the remote control) and/or communicate the data between the recharging unit and another device.

Referring to FIG. 13b, a block diagram of another exemplary system in which the energy and data are transferred from a recharging unit 30 to a dispensing unit 10 using one transmission signal is shown. The battery charger signal generator 305 is configured to generate a carrier wave that provides the energy signal (e.g., a high power current). The carrier signal is modulated such that a higher frequency data signal is superimposed on the carrier signal using the transceiver 3101. The dispensing unit 10 includes high and low pass filters 162 and 172, respectively, that selectively enable data and power to reach the transceiver 1601 and DC charger 1701, respectively.

In some embodiments, other techniques, such as zero-crossing techniques, pulse modulation, phase modulation, amplitude modulation or frequency modulation, may be used to transfer data and/or energy between the recharging unit 30 and the dispensing unit 10.

In some embodiments, at least one coil is included in one or more units (e.g., the dispensing unit 10, the recharging unit 30 and a remote control unit 40) to provide wireless magnetic communication over longer distances (e.g., 30 cm and longer), as described, for example, in U.S. Pats. Nos. 5,771, 438, 5,912,925, 5,982,764, 6,459,882, 7,142,811 and 7,254, 366, the contents of all of which are hereby incorporated by reference in their entireties.

Referring to FIGS. 14a to 14e, views and diagrams depicting an exemplary procedure to enable replacement of a depleted reusable part 100b with a charged reusable part 100a is illustrated.

Figure 14A:
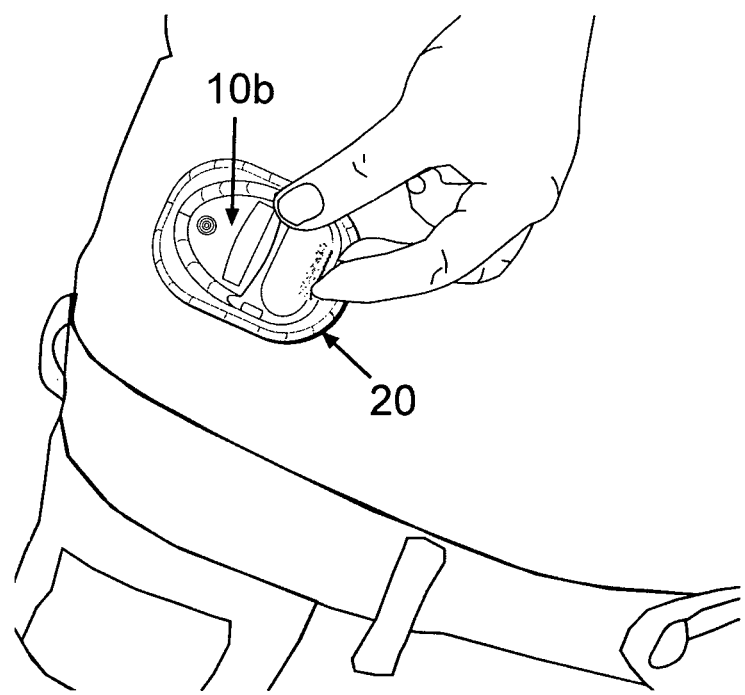

In particular, FIG. 14a shows a dispensing unit 10b detachably connected to the user via a cradle unit 20. A cradle unit such as the one shown in FIG. 14a is also described in co-owned/co-pending U.S. Ser. No. 12/004,837, filed on the Dec. 20, 2007, the content of which is hereby incorporated by reference in its entirety.

Figure 14B:
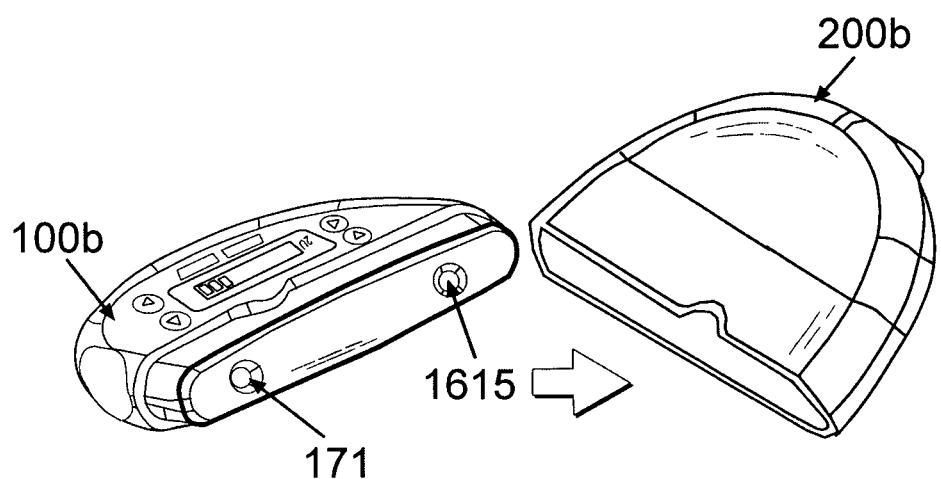

FIG. 14b shows a disposable part 200b and a reusable part 100b. The reusable part 100b includes two connectors: a power connector 171 and a data connector 1615. When the reusable part and the disposable part are set apart, the connectors 171 and 1615 are exposed and the reusable part 100b can thus be connected to the recharging unit 30, as shown in FIG. 14c.

FIG. 14c shows a recharging unit 30 that includes two sets of connectors (denoted as a and b), each of which includes a data plug (3105a and 3105b, respectively) and a power plug (3055a and 3055b, respectively), enabling simultaneously charging of two different reusable parts (100a and 100b, respectively). As shown in FIG. 14c, a charged reusable part 100a is already connected to recharging unit 30 at the time that a depleted reusable part 100b is about to be connected. Also detachably connected to the recharging unit 30 via a USB plug 3801 is a personal computer (PC) 50 (e.g., an iMac™ commercially available by Apple Inc., USA), which provides power to the recharging unit 30, and also provides data processing and storage functionalities to enable data management of the dispensing units connected to the recharging unit 30. An indication device, e.g., a display 340 (e.g., LCD) provides information and indications regarding the status of the connections, power transfer, data transfer and the like. Such information may also be displayed on the PC 50. In some embodiments, the PC 50 may be a laptop, iPod, cellular phone or any other wire/wireless electronic device which includes memory and/or processor.

Figure 14D:
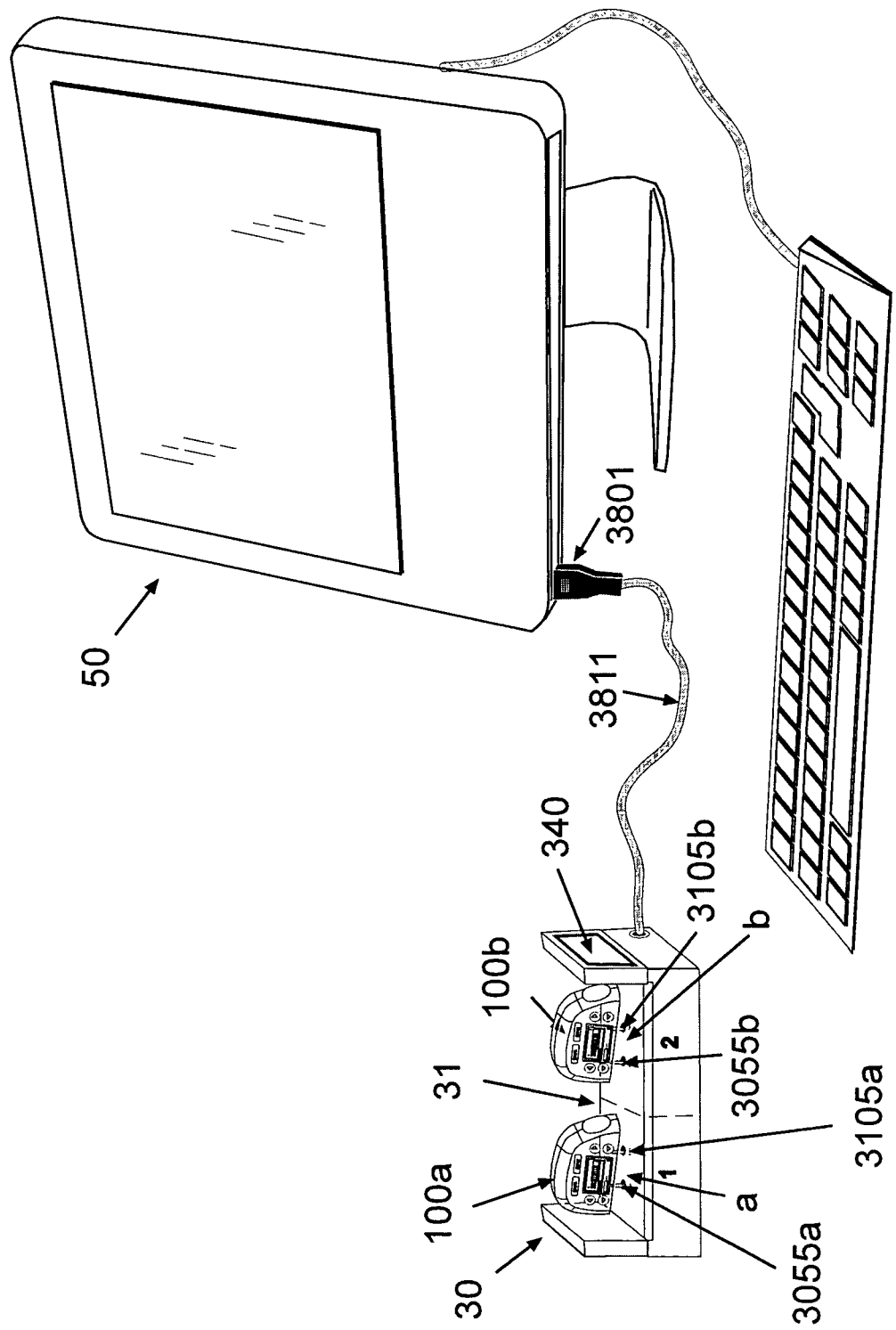

FIG. 14d shows the two separate reusable parts 100a and 100b mechanically (and electrically) connected simultaneously to the recharging unit 30. The connection between the two reusable parts 100a and 100b can be used to transfer data between them. For example, flow delivery programs update (e.g., basal and bolus profiles, etc.) can be transferred from the depleted reusable part 100b to the recharged reusable part 100a, thus preserving data and delivery profiles used by the user, and enabling the user to avoid having to re-program the charged reusable part 100a.

Figure 14E:
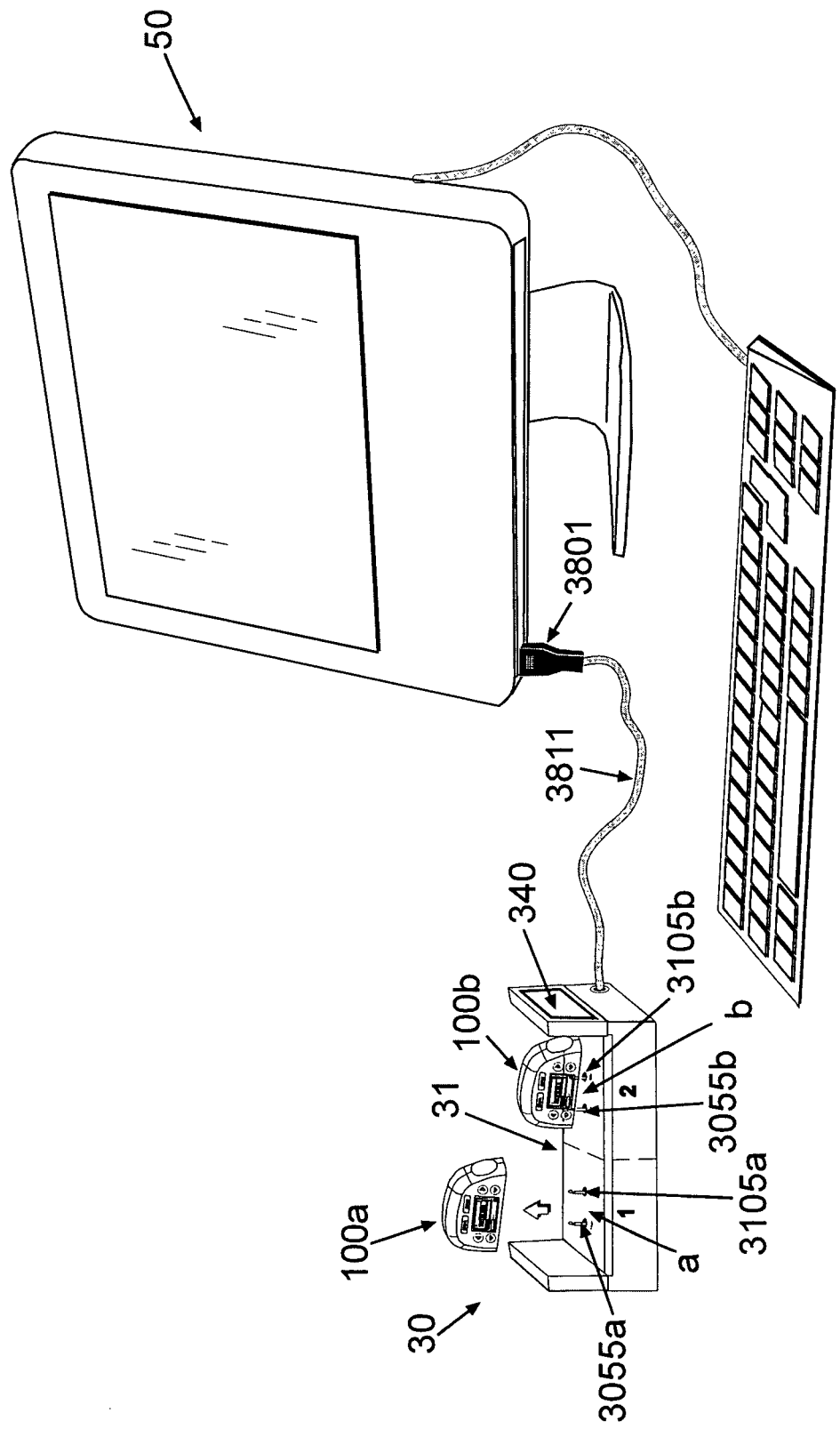

FIG. 14e shows the final stage of reusable part 100a replacement. The depleted part 100b is recharged by the recharging unit 30 and the charged and updated reusable part 100a is disconnected from the recharging unit 30. The charged and updated reusable part 100a may then be connected to a disposable part, and the assembled dispensing unit can be attached, for example, to the cradle 20 (shown in FIG. 14a).

Referring to FIGS. 15a-b, diagrams depicting an exemplary recharging unit 30 connectable to a remote control unit 40 and to a pair of reusable parts 100a and 100b are shown. The remote control unit 40 (a magnified view of which is shown in FIG. 15b) includes electrical connectors 42 to enable electrical connection to the recharging unit 30 set of connectors 3955. Connecting the remote control unit 40 to the recharging unit 30 enables charging the remote control unit 40 and/or providing a two-way communication with all the connected units, namely, the reusable parts 100a and 100b, the recharging unit 30 and a USB/remote host 50.

Figure 16A:
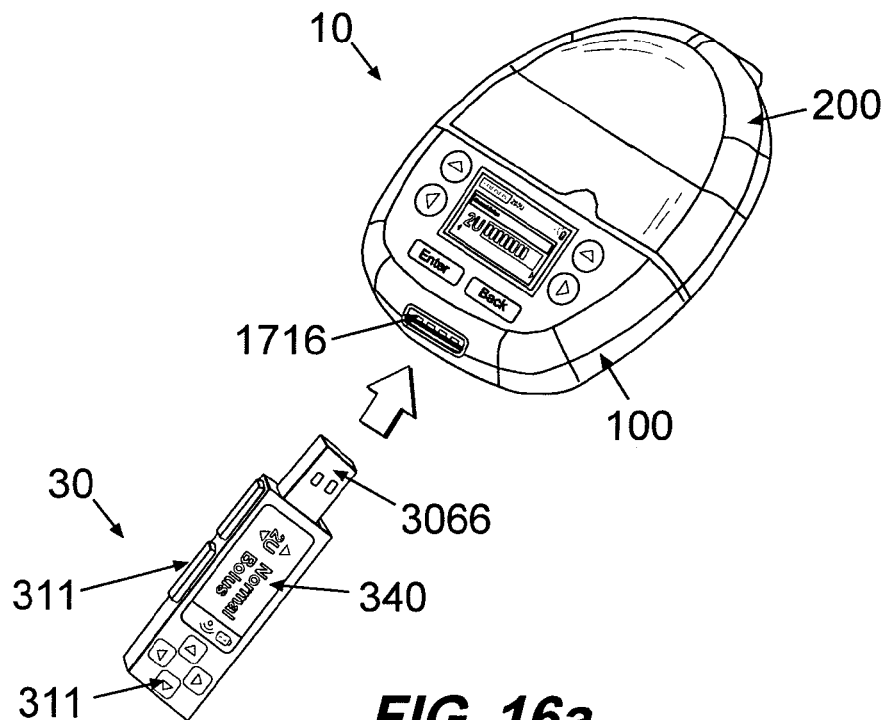
FIGS. 16a-b are views of an exemplary dispensing unit and a portable recharging and controlling unit.
Figure 16B:
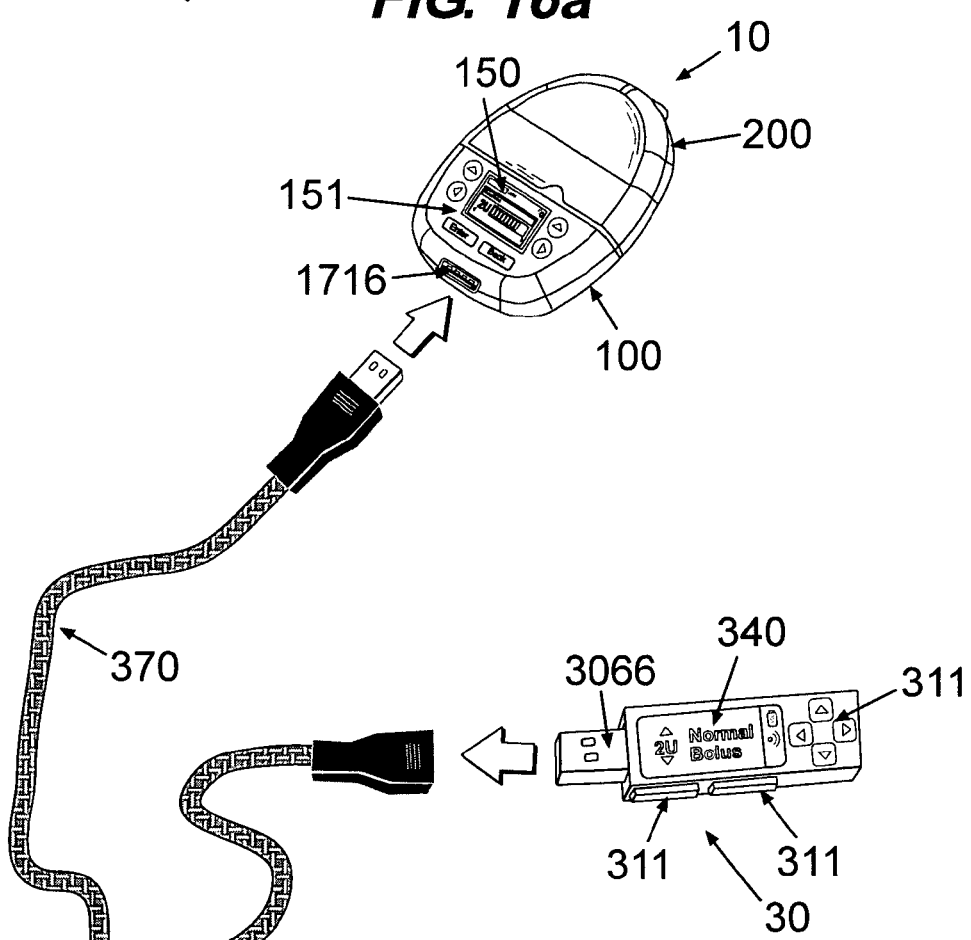

Referring to FIGS. 16a and 16b, views of an exemplary portable recharging unit 30 that can also control the dispensing unit 10 are shown. The recharging unit 30 includes an indication device 340 (e.g., an LCD) and a user input interface 311 (e.g., a keypad and/or operating buttons/switches). The recharging unit also includes data and energy transfer mechanism implemented, for example, using a USB plug 3066 connectable to a dispensing unit 10. The dispensing unit 10 does not require an indication device or user input interface (because those may already be provided through the recharging unit 30) and therefore manufacture of the dispensing unit may be performed in a more cost efficient manner. Alternatively, in some embodiments, the dispensing unit connectable to the recharging unit 30, as shown in FIG. 16a, may also have a separate indication device 150 and a separate user input interface 151 disposed on the housing of the dispensing unit 10 (as shown in FIG. 16b). The user inputs received by the user input interface 311 of the recharging unit are transferred to the dispensing unit 10. Communication between the dispensing unit 10 and the recharging unit 30 is established upon plugging the USB plug 3066 to the USB socket 1716 directly or through an extension cord 370 (as shown in FIG. 16b). In some embodiments, wireless communication between the portable recharging unit 30 and the dispensing unit 10 may be implemented by including wireless communication modules (e.g., RF transceivers) in both units.

Figure 17:
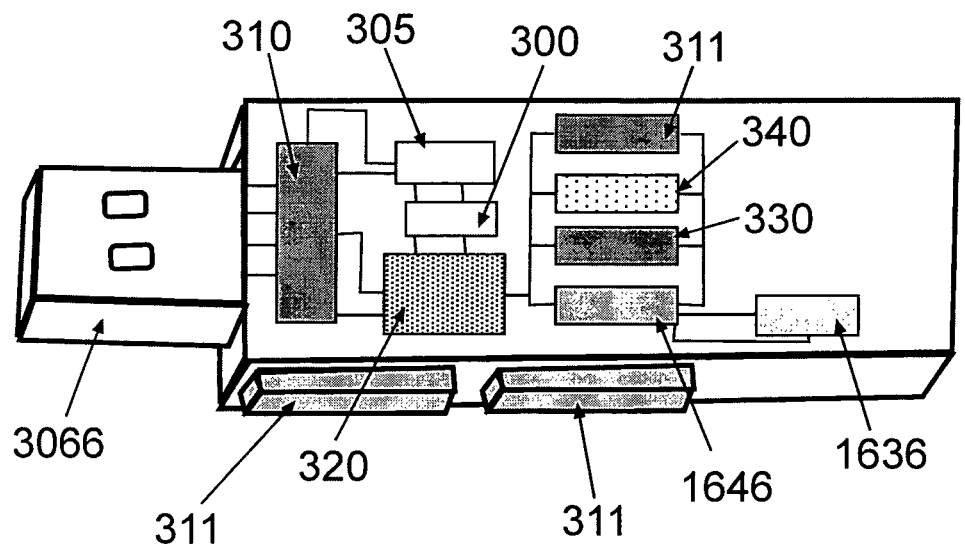
FIG. 17 is a diagram depicting an exemplary interior configuration of a portable recharging and controlling unit.

Referring to FIG. 17, a diagram of an exemplary portable rechargeable unit is shown. The portable rechargeable unit includes:

A USB plug 3066 connected to a communication module 310, e.g. a USB interface that enables sending and receiving data and energy.

A processor 320 to control the operation of the rechargeable unit.

A charger 305 for recharging the internal rechargeable energy storage cell 300. The charger 305 charges the internal energy storage cell 300 (which may include one or more rechargeable batteries) when connected to a voltage of, for example, 5 v or higher (as provided by standard USB host). In some embodiments, when the charger 305 is connected to a voltage source outputting a voltage level below some pre-determined threshold, e.g., 3 v or lower, it supplies power from energy storage cell 300 to the dispensing unit. Alternatively, in some embodiments, the portable rechargeable unit can include one or more replaceable power sources, such as button size batteries or AAA batteries.

The recharging unit 30 may also includes a data storage module 330 to store software, user information, fluid delivery profiles such as basal profiles (amounts of drug to be delivered in specified time periods), etc. A User input interface 311, an indication device 340 and an RF transceiver 1646 with an antenna 1636 to enable wireless communication may also be provided.

Figure 18A:
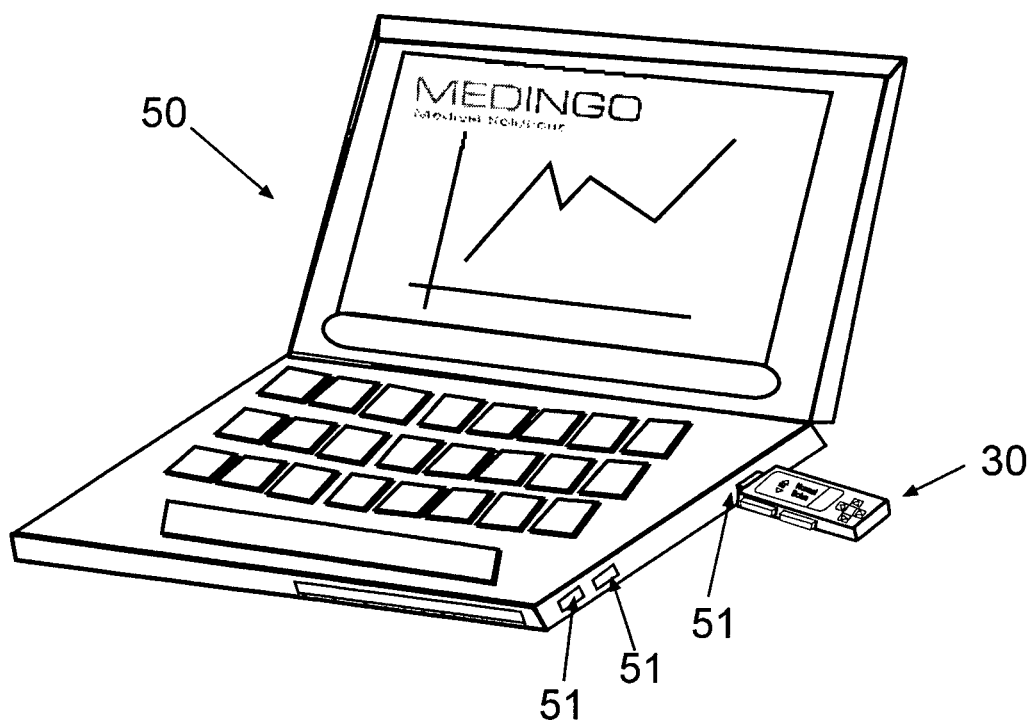
FIGS. 18a-b are diagrams showing exemplary data transfer implementations between a portable recharging and controlling unit, a PC and a dispensing unit.

FIG. 18a is a diagram showing a recharging unit 30 connected to USB socket 51 of a personal computer (PC) 50, for recharging its internal energy storage cell and/or for data transfer.

Figure 18B:
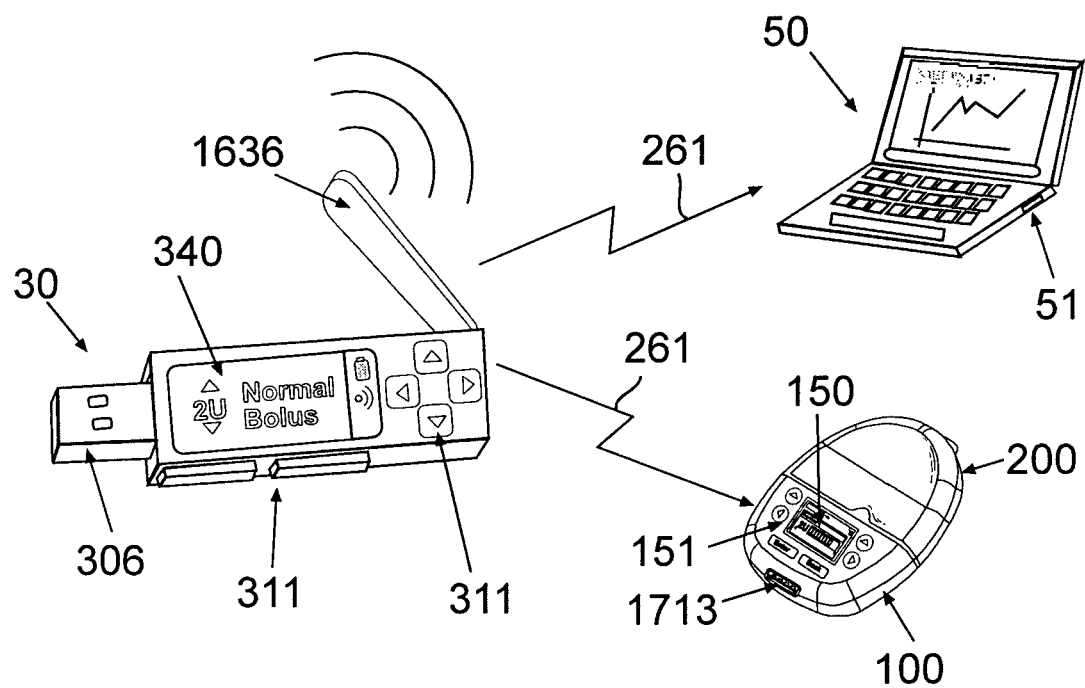

FIG. 18b is a diagram showing an RF communication link 261 established between a recharging unit 30, a personal computer (PC) 50 and a dispensing unit 10. The dispensing unit 10 is connectable to the recharging unit 30 and/or to the PC 50 and can also receive commands via the RF communication link 261 and/or operating buttons 151.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

What is claimed is:

1. A therapeutic fluid delivery system comprising:
a pump dispensing therapeutic fluid to the body of a user, the pump including a disposable part and a reusable part connectable to the disposable part, the reusable part including one or more first transducers and one or more rechargeable batteries for storing energy to power the pump; and
a recharging device configured to recharge the reusable part, the charging device including one or more second transducers for inductively transferring electrical power to the reusable part through the one or more first transducers;
wherein die electrical power inductively transferred to the reusable part includes a power signal modulated based on data relating to operation of the pump, and the reusable part further includes a communication module to demodulate and determine, based on the modulated power signal from the recharging device, the data relating to the operation of the pump.

2. The system of claim 1, wherein the pump comprises at least one additional reusable part connectable to the disposable part.

3. The system of claim 1, wherein the reusable parts are configured to be interchangeable with one another.

4. The system of claim 1, wherein:
the disposable part includes a reservoir containing the therapeutic fluid;
the reusable part further includes parts having at least a portion of a driving mechanism to cause delivery of the therapeutic fluid from the reservoir to the user's body, and at least one electrical connector coupleable to the recharging device when the reusable part is disconnected from the disposable part to direct electrical power received from the recharging device to recharge the one or more rechargeable batteries; and the pump is operable upon connection of the disposable part and the reusable.

5. The system of claim 1, wherein:

the reusable part further includes at least one first electric connector, the recharging device comprises at least one second electrical connector coupleable with the at least one first electrical connector of the reusable part to provide electrical power to recharge the one or more rechargeable batteries; and a charger configured to direct electrical power from a power source to the at least one second electrical connecter of the recharging device, said charger being further configured to alter the electrical power directed from the power source.

6. The system of claim 1, wherein the reusable part further comprises a communication module to communicate data signals representative of data relating to operation of the pump, the communication module being configured to communicate the data signals substantially concomitantly with receipt of the electrical power from the recharging device.

7. The system of claim 6, wherein the at least one first electrical connector of the reusable part includes a USB connector configured to direct the electrical power and the data signals.

8. The system of claim 6, wherein the communication module includes a wireless transceiver and is further configured to establish a communication link with a remote control communicating the data signals.

9. The system of claim 1, wherein the at least one first electrical connector of the reusable part includes:

at least one dedicated recharging electrical terminal to receive the electrical power from the recharging device; and at least one dedicated data terminal to perform bi-directional communication of data relating to operation of the pump.

10. The system of claim 1, further comprising a cradle configured to be adhered to the skin of the user, the pump being connectable and disconnectable to and from the cradle.

11. The system of claim 5, wherein the recharging device further comprises a communication module to communicate data signals representative of data relating to operation of the pump, and the at least one second electrical connector of the recharging device is configured to provide the electrical power substantially concomitantly with communication of the data signals through the communication module of the recharging device.

12. The system of claim 5, wherein the at least one second electrical connector of the recharging device includes a first recharging electrical connector configured to be coupled to the reusable and a second recharging electrical connector configured to be coupled to another reusable part.

13. The system of claim 11, wherein the communication module of the recharging device is configured to receive data from the reusable part and transmit the received data to another reusable part.

14. The system of claim 5, wherein the recharging device further comprising a storage device to store data relating to operation of the pump.

15. The system of claim 1, wherein the recharging device is further configured to charge a remote control and/or communicate data signals with the remote control.

16. The system of claim 11, wherein the communication module of the recharging device is configured to communicate data signals with at least one of a pump, a personal computer and a remote control.

17. The system of claim 5, wherein the at least one second electrical connector of the recharging device includes:

at least one recharging electrical terminal to direct output power from the power source; and at least one data terminal to communicate data signals representative of the data relating to operation of the pump.

18. The system of claim 5, wherein the recharging device further comprises a portable power source including at least one battery to generate at least a portion of the electrical power directed to the reusable part.

19. The system of claim 5, wherein the recharging device further comprises a portable housing containing the at least one second electrical connector of the recharging device such that the at least one second electrical connector in the portable housing is configured to be coupled to the reusable part while the pump is operating.

20. The system of claim 1, wherein the pump is configured to perform one or more of dispensing the therapeutic fluid to the user and sensing analyte levels of the user while the one or more batteries are charged by the recharging device.

21. The system of claim 5, wherein the recharging device is configured to operate in accordance with EN-IEC 60602 standard.

22. A therapeutic fluid delivery device comprising:

a disposable part having a reservoir containing the therapeutic fluid; and a reusable part comprising at least a portion of the driving mechanism to cause delivery of the therapeutic fluid from the reservoir to a user's body, one or more rechargeable batteries and one or more transducers;

wherein:

the device is operable upon connection of the disposable part and the reusable part; and the reusable part is coupleable to a recharging device receive a power signal modulated based on data relating to operation of the device, the reusable device being configured to demodulate and determine, based on the modulated power signal, the data relating to the operation of the pump.

23. The device of claim 22, wherein the reusable part is configured to be accessible by the recharging device when the reusable part is disconnected from the disposable part to receive electrical power from the recharging device to charge the one or more rechargeable batteries.

24. The device of claim 22, wherein the reusable part comprises at least two or more of the reusable part, the at least two or more reusable parts being configured to be interchangeable with one another such that while at least one of the two or more reusable parts is connected to the recharging device another reusable part of the two or more reusable parts is connected to the disposable part and the device is operating.

25. The device of claim 22, wherein the device is waterproof.

* * * * *